United States Patent [19]

Drayna et al.

[11] Patent Number: 5,364,934
[45] Date of Patent: Nov. 15, 1994

[54] PLASMA CARBOXYPEPTIDASE

[75] Inventors: Dennis T. Drayna, San Francisco; Dan L. Eaton, San Rafael, both of Calif.

[73] Assignee: Genentech, Inc., South San Francisco, Calif.

[21] Appl. No.: 167,727

[22] Filed: Dec. 15, 1993

Related U.S. Application Data

[60] Continuation of Ser. No. 959,944, Oct. 14, 1992, abandoned, which is a division of Ser. No. 649,591, Feb. 1, 1991, Pat. No. 5,201,161.

[51] Int. Cl.$^5$ .................. C12N 15/57; C12N 1/21; C12N 5/10; C12N 15/63
[52] U.S. Cl. .................. 536/23.2; 435/240.2; 435/252.3; 435/320.1
[58] Field of Search .................. 536/23.2; 435/252.3, 435/240.2, 320.1

[56] References Cited

U.S. PATENT DOCUMENTS 4,631,270 12/1986 Yankeelov et al. .................. 514/15

OTHER PUBLICATIONS

Yamamoto, K. K. et al.; J. Biol. Chem. 267:2575–2581 (Feb. 1992).
Skidgel, R. A. et al.; Arch. Biochem. Biophys. 267:660–667 (1988).
Tsai, S. P. et al.; Genomics 14:549–550 (1992).
Eaton, D. L. et al.; J. Biol. Chem. 266:21,833–21,838 (1991).
Plummer et al., "Human Plasma Carboxypeptidase N", J. Biol. Chem., 253(11): 3907–3912 (1978).
Levin et al., "Isolation and characterization of the subunits of human plasma carboxypeptidase N (kininase I)", Proc. Natl. Acad. Sci., 79(15): 4618–4622 (1982).
Blass et al., "In vitro protaminase activity of human plasma and serum and the human carboxypeptidase N", Pathol Biol., 28(8): 527–534, in Chem. Abst., 94(1): 1477 Abst. No. 1475m (1980).
Skidgel et al., "Amino Acid Sequence of the N-Terminus and Selected Tryptic Peptides of the Active Subunit of Human Plasma Carboxypeptidase N: Comparison with Other Carboxypeptidases", Biochem. & Biophus. Res. Comm., 154(3): 1323–1329 (1988).
Oshima et al. "Subunits of Human Plasma Carboxypeptidase N (Kininase I; Anaphylatoxin Inactivator)", Biochim. Biophys. Acta, 365: 344–348 (1974).
Oshima et al. "Plasma Carboxypeptidase N, Subunits and Characteristics", Archives of Biochem & Biophys., 170:132–138 (1975).
Juillerat-Jeanneret et al., "Some Properties of Porcine Carboxypeptidase N", Hoppe-Seyler's Z. Physiol. Chem., 363(1): 51–58 (1982).
Lavras et al., "The kininases of Bothrups jararaca plasma", Acta Physiol. Latinoam, 30(4): 269–274 in in Chem. Abst., 95(1): 2422, Abst. No. 2413 (1980).
Wade et al., "The amino acid sequence of the activation peptide of bovine pro-carboxypeptidase A", Biochimie, 70: 1137–1142 (1988).
Pannell et al., "Complementary Modes of Action of Tissue-type Plasminogen Activator and Pro-urokinase by by which Their Synergistic Effect on Clot Lysis May Be Explained", J. Clin. Invest., 81: 853–859 (1988).
Vendrell et al., "Primary Structure of the Activation Segment of Procarboxypeptidase A from Porcine Pan-
(List continued on next page.)

Primary Examiner—Robert A. Wax
Assistant Examiner—Eric Grimes
Attorney, Agent, or Firm—Janet E. Hasak

[57] ABSTRACT

A novel polypeptide, designated plasma carboxypeptidase B (PCPB), has been purified from human plasma. It has been cloned from a human liver cDNA library using PCR amplification. Provided herein is nucleic acid encoding PCPB useful in diagnostics and in the recombinant preparation of PCPB. PCPB is used in the preparation and purification of antibodies thereto, in the purification of plasminogen, in the inhibition of plasminogen activation by t-PA in the presence of fibrinogen, and in diagnostic assays.

5 Claims, 9 Drawing Sheets

OTHER PUBLICATIONS creas", *Biochem and Biophys. Res. Comm.*, 141(2): 517–523 (1986).

Aviles et al., "Sequential Homologies between Procarboxypeptidases A and B from Porcine Pancreas", *Biochem and Biophys. Res. Comm.*, 130(1): 97–103 (1985).

Everitt and Neurath, "Rat Peritoneal Mast Cell Carboxypeptidase: Localization, Purification, and Enzymatic Properties", *FEBS Letters*, 110(2): 292–296 (1980).

Schwartz et al., "Localization of Carboxypeptidase A to the Macromolecular Heparin Proteoglycan–Protein Complex in Secretory Granules of Rat Serosal Mast Cells", *J. Immunol.*, 128(3): 1128–1133 (1982).

Serafin et al., "Carboxypeptidase A in Mouse Mast Cells: Identification, Characterization and Use as a Differentiation Marker", *J. Immunol.*, 139: 3771–3776 (1987).

Reynolds et al., "Immortalization of Murine Connective Tissue-type Mast Cells at Multiple Stages of their Differentiation by Coculture of Splenocytes with Fibroblasts that Produce Kirsten Sarcoma Virus", *J. Biol. Chem.* 263(25): 12783–12791 (1988).

Goldstein et al., "Human Mast Cell Carboxypeptidase: Purification and Characterization", *J. Clin. Invest.*, 83: 1630–1636 (1989).

Goldstein et al., "Detection and Partial Characterization of a Human Mast Cell Carboxypeptidase", *J. Immunol.*, 139(8): 2724–2729 (1987).

Kokkonen et al., "Proteolytic Enzymes of Mast Cell Granules Degrade Low Density Lipoproteins and Promote Their Granule-mediated Uptake by Macrophages in Vitro", 264(18): 10749–10755 (1989).

Kokkonen et al. "Low Density Lipoprotein Degradation by Secretory Granules of Rat Mast Cells", 261(34): 16067–16072 (1986).

Delk et al., "Radioimmunoassay of Active Pancreatic Enzymes in Sera from Patients with Acute Pancreatitis. I. Active Carboxypeptidase B", *Clin. Chem.* 31(8):1294–1300 (1985).

Reeck and Neurath, "Isolation and Characterization of Pancreatic Procarboxypeptidase B and Carboxypeptidase B of the African Lungfish", *Biochemistry*, 11(21): 3947–3955 (1972).

Titani et al., "Amino-Acid Sequence of Bovine Carboxypeptidase B", *Proc. Natl. Acad. Sci USA*, 72(5): 1666–1670 (1975).

Bradshaw et al., "Amino Acid Sequence of Bovine Carboxypeptidase A. Isolation and Characterization of Selected Peptic and Nagarse Peptides and the Complete Sequence of Fragment F", *Biochemistry*, 10(6): 961–971 (1971).

Gardell et al., "A Novel Rat Carboxypeptidase, CPA2: Characterization, Molecular Cloning and Evolutionary Implications on Substrate Specificity in the Carboxypeptidase Gene Family", *J. Biol. Chem.*, 263(33): 17828–17836 (1988).

Clauser et al., "Structural Characterization of the Rat Carboxypeptidase A1 and B Genes", *J. Biol. Chem.* 263(33): 17837–17845 (1988).

Reynolds et al., "Isolation and Molecular Cloning of Mast Cell Carboxypeptidase A: A Novel Member of the Carboxypeptidase Gene Family", *J. Biol. Chem.*, 264(33): 20094–20099 (1989).

Tan et al., "The Deduced Protein Sequence of the Human Carboxypeptidase N High Molecular Weight Subunit Reveals the Presence of Leucine-rich Tandem Repeats", *J. Biol. Chem.*, 265(1): 13–19 (1990).

Gebhard et al., "cDNA cloning and complete primary structure of the small, active subunit of human carboxypeptidase N (kininase 1)", *Eur. J. Biochem.*, 178: 603–607 (1989).

Valls et al., "Protein Sorting in Yeast: the Localization Determinant of Yeast Vacuolar Carboxypeptidase Y Resides in the Propeptide", *Cell*, 48: 887–897 (1987).

Titani et al., "Amino Acid Sequence of Crayfish (*Astacus fluviatilis*) Carboxypeptidase B", *Biochemistry*, 23: 1245–1250 (1984).

Quinto et al., "Rat preprocarboxypeptidase A: cDNA sequence and preliminary characterization of the gene", *Proc. Natl. Acad. Sci USA*, 79: 31–35 (1982).

Reynolds et al., "Cloning of cDNAs that encode human mast cell carboxypeptidase A, and comparison of the protein with mouse mast cell carboxypeptidase A and rat pancreatic carboxypeptidases", *Proc. Natl. Acad. Sci. USA*, 86: 9480–9484 (1989).

McDonald and Barrett, *Mammalian Proteases: A Glossary and Bibliography*, vol. 2–Exopeptidases, Academic Press, Academic Press, pp. 155–224 (1986).

Fricker et al., "Isolation and Sequence Analysis of (List continued on next page.)

OTHER PUBLICATIONS cDNA for Rat Carboxypeptidase E [EC 3.4.17.10], A Neuropeptide Processing Enzyme", *Mol. Endocrin.*, 3(4): 666–673 (1989).

Baulcombe et al., "A Gibberellin Responsive Wheat Gene Has Homology to Yeast Carboxypeptidase Y", *J. Biol. Chem.*, 262(28): 13726–13735 (1987).

Manser et al., "Human carboxypeptidase E", *Biochem. J.*, 267: 517–525 (1990).

Tan et al., "Molecular Cloning and Sequencing of the cDNA for Human Membrane-bound Carboxypeptidase M", *J. Biol. Chem.*, 264(22): 13165–13170 (1989).

Svendsen et al., "Amino Acid Sequence of Carboxypeptidase Y. II. Peptides from Enzymatic Cleavages", *Carlsberg Res. Commun.*, 47: 15–27 (1982).

Sorenson et al., "Primary Structure of Carboxypeptidase II from malted barley", *Carlsberg Res. Commun.*, 52: 285–295 (1987).

Folk & Gladner, "Carboxypeptidase B: I. Purification of the Zymogen and Specificity of the Enzyme", *J. Biol. Chem.*, 231: 379–391 (1958).

```
AGCTCGTCGA CCTTTCTCTG AAGAGAAAAT TGCTGTTGGG ATG AAG  46
                                              Met Lys
                                              -22

CTT TGC AGC CTT GCA GTC CTT GTA CCC ATT GTT CTC TTC  85
Leu Cys Ser Leu Ala Val Leu Val Pro Ile Val Leu Phe
-20             -15             -10

TGT GAG CAG CAT GTC TTC GCG TTT CAG AGT GGC CAA GTT  124
Cys Glu Gln His Val Phe Ala Phe Gln Ser Gly Gln Val
        -5              -1 ↑ 1              5

1<--------------- 46-bp probe -----------
CTA GCT GCT CTT CCT AGA ACC TCT AGG CAA GTT CAA GTT  163
Leu Ala Ala Leu Pro Arg Thr Ser Arg Gln Val Gln Val
            10                  15

------------------>1
CTA CAG AAT CTT ACT ACA ACA TAT GAG ATT GTT CTC TGG  202
Leu Gln Asn Leu Thr Thr Thr Tyr Glu Ile Val Leu Trp
20                  25                  30

CAG CCG GTA ACA GCT GAC CTT ATT GTG AAG AAA AAA CAA  241
Gln Pro Val Thr Ala Asp Leu Ile Val Lys Lys Lys Gln
            35              40                  45

GTC CAT TTT TTT GTA AAT GCA TCT GAT GTC GAC AAT GTG  280
Val His Phe Phe Val Asn Ala Ser Asp Val Asp Asn Val
                50              55

AAA GCC CAT TTA AAT GTG AGC GGA ATT CCA TGC AGT GTC  319
Lys Ala His Leu Asn Val Ser Gly Ile Pro Cys Ser Val
        60              65                  70

TTG CTG GCA GAC GTG GAA GAT CTT ATT CAA CAG CAG ATT  358
Leu Leu Ala Asp Val Glu Asp Leu Ile Gln Gln Gln Ile
                75              80

TCC AAC GAC ACA GTC AGC CCC CGA GCC TCC GCA TCG TAC  397
Ser Asn Asp Thr Val Ser Pro Arg Ala Ser Ala Ser Tyr
85              90      ↑↑↑             95

TAT GAA CAG TAT CAC TCA CTA AAT GAA ATC TAT TCT TGG  436
Tyr Glu Gln Tyr His Ser Leu Asn Glu Ile Tyr Ser Trp
        100             105                 110
```

FIG. 4A

```
ATA GAA TTT ATA ACT GAG AGG CAT CCT GAT ATG CTT ACA  475
Ile Glu Phe Ile Thr Glu Arg His Pro Asp Met Leu Thr
                115             120

AAA ATC CAC ATT GGA TCC TCA TTT GAG AAG TAC CCA CTC  514
Lys Ile His Ile Gly Ser Ser Phe Glu Lys Tyr Pro Leu
        125             130             135

TAT GTT TTA AAG GTT TCT GGA AAA GAA CAA ACA GCC AAA  553
Tyr Val Leu Lys Val Ser Gly Lys Glu Gln Thr Ala Lys
            140             145

AAT GCC ATA TGG ATT GAC TGT GGA ATC CAT GCC AGA GAA  592
Asn Ala Ile Trp Ile Asp Cys Gly Ile His Ala Arg Glu
150         155             160

TGG ATC TCT CCT GCT TTC TGC TTG TGG TTC ATA GGC CAT  631
Trp Ile Ser Pro Ala Phe Cys Leu Trp Phe Ile Gly His
        165             170             175

ATA ACT CAA TTC TAT GGG ATA ATA GGG CAA TAT ACC AAT  670
Ile Thr Gln Phe Tyr Gly Ile Ile Gly Gln Tyr Thr Asn
            180             185

CTC CTG AGG CTT GTG GAT TTC TAT GTT ATG CCG GTG GTT  709
Leu Leu Arg Leu Val Asp Phe Tyr Val Met Pro Val Val
        190             195             200

AAT GTG GAC GGT TAT GAC TAC TCA TGG AAA AAG AAT CGA  748
Asn Val Asp Gly Tyr Asp Tyr Ser Trp Lys Lys Asn Arg
            205             210

ATG TGG AGA AAG AAC CGT TCT TTC TAT GCG AAC AAT CAT  787
Met Trp Arg Lys Asn Arg Ser Phe Tyr Ala Asn Asn His
215             220             225

TGC ATC GGA ACA GAC CTG AAT AGG AAC TTT GCT TCC AAA  826
Cys Ile Gly Thr Asp Leu Asn Arg Asn Phe Ala Ser Lys
        230             235             240

CAC TGG TGT GAG GAA GGT GCA TCC AGT TCC TCA TGC TCG  865
His Trp Cys Glu Glu Gly Ala Ser Ser Ser Ser Cys Ser
            245             250

GAA ACC TAC TGT GGA CTT TAT CCT GAG TCA GAA CCA GAA  904
Glu Thr Tyr Cys Gly Leu Tyr Pro Glu Ser Glu Pro Glu
        255             260             265
```

FIG. 4B

```
GTG AAG GCA GTG GCT AGT TTC TTG AGA AGA AAT ATC AAC 943
Val Lys Ala Val Ala Ser Phe Leu Arg Arg Asn Ile Asn
            270             275

CAG ATT AAA GCA TAC ATC AGC ATG CAT TCA TAC TCC CAG 982
Gln Ile Lys Ala Tyr Ile Ser Met His Ser Tyr Ser Gln
280             285                     290

CAT ATA GTG TTT CCA TAT TCC TAT ACA CGA AGT AAA AGC 1021
His Ile Val Phe Pro Tyr Ser Tyr Thr Arg Ser Lys Ser
            295                 300             305

AAA GAC CAT GAG GAA CTG TCT CTA GTA GCC AGT GAA GCA 1060
Lys Asp His Glu Glu Leu Ser Leu Val Ala Ser Glu Ala
                310                 315

GTT CGT GCT ATT GAG AAA ACT AGT AAA AAT ACC AGG TAT 1099
Val Arg Ala Ile Glu Lys Thr Ser Lys Asn Thr Arg Tyr
320             325                     330

ACA CAT GGC CAT GGC TCA GAA ACC TTA TAC CTA GCT CCT 1138
Thr His Gly His Gly Ser Glu Thr Leu Tyr Leu Ala Pro
            335                 340

GGA GGT GGG GAC GAT TGG ATC TAT GAT TTG GGC ATC AAA 1177
Gly Gly Gly Asp Asp Trp Ile Tyr Asp Leu Gly Ile Lys
345             350                     355

TAT TCG TTT ACA ATT GAA CTT CGA GAT ACG GGC ACA TAC 1216
Tyr Ser Phe Thr Ile Glu Leu Arg Asp Thr Gly Thr Tyr
        360                 365             370

GGA TTC TTG CTG CCG GAG CGT TAC ATC AAA CCC ACC TGT 1255
Gly Phe Leu Leu Pro Glu Arg Tyr Ile Lys Pro Thr Cys
                375                 380

AGA GAA GCT TTT GCC GCT GTC TCT AAA ATA GCT TGG CAT 1294
Arg Glu Ala Phe Ala Ala Val Ser Lys Ile Ala Trp His
385             390                     395

GTC ATT AGG AAT GTT T AATGCCCTG ATTTTATCAT TCTGCTTCCG 1340
Val Ile Arg Asn Val
            400 401

TATTTTAATT TACTGATTCC AGCAAGACCA AATCATTGTA TCAGATTATT 1390

TTTAAGTTTT ATCCGTAGTT TTGATAAAAG ATTTTCCTAT TCCTTGGTTC 1440

TGTCAGAGAA CCTAATAAGT GCTACTTTGC CATTAAGGCA GACTAGGGTT 1490
```

FIG. 4C

```
CATGTCTTTT TACCCTTTAA AAAAAAATTG TAAAAGTCTA GTTACCTACT 1540

TTTTCTTTGA TTTTCGACGT TTGACTAGCC ATCTCAAGCA ACTTTCGACG 1590

TTTGACTAGC CATCTCAAGC AAGTTTAATC AAAGATCATC TCACGCTGAT 1640

CATTGGATCC TACTCAACAA AAGGAAGGGT GGTCAGAAGT ACATTAAAGA 1690

TTTCTGCTCC AAATTTTCAA TAAATTTCTT CTTCTCCTTT AAAAAAAAAA 1740

AAAAAAAAA 1749
```

```
hpcpb  295 FLRRNINQIKAYISMHSYSQHIVFPYSYTRSKSKDHEELSLVASEAVRAI
rcpb   268 FIRNNLSTIKATLTIHSYSQMMLYPYSYDYKLPENYEELNALVKGAKEL
rtcpa  292 FVTSH-GNIKAFISIHSYSQLLLYPYGYTSEPAPDQAELDQLAKSAVTAL
hmccpa 289 FIRSHLNEIKVYITFHSYSQMLFPYGYTSKLPPNHEDLAKVAKIGTDVL
mmccpa 289 FIRSHLNSIKAYITFHSYSQMLIPPYGYTFKLPPNHQDLLKVARIATDAL
rtcpa2 290 FIKSH-GKVKAFITLHSYSQLLMFPYGYKCTKPDDFNELDEVAQKAAQAL hpcpb  345 EKTSKNTRYTHGHGSETLYLAPGGGDDWIYDLGIKYSFTIELRDTGTYGF
rcpb   318 -ATLHGTKYTYEPGATTIYPAAGGSDDWSYDQGIKYSFTFELRDTGFFGF
rtcpa  341 -TSLHGTEFKYGSIIDTIYQASGSTIDWTYSQGIKYSFTFELRDTGFFGF
hmccpa 339 -STRYETRYIYGPIESTIYPISGSSLDWAYDLGIKHTFAFELRDTGLRGF
mmccpa 339 -STRYETRYIYGPIASTIYKTSGSSLDWAYDLGIKHTFAFELRDKGKFGF
rtcpa2 339 -KRLHGTSYKVGPICSVIYQASGGSIDWAYDLGIKYSFAFELRDTAFYGF hpcpb  395 LLPERYIKPTCREAFAVSKIAWHVIRNV-
rcpb   367 LLPESQIRQTCEETMLAVKYIANYVREHLY
rtcpa  390 LLPASQIIPTAEETWLALLTIMDHTVKHPY
hmccpa 388 LLPESRIKPTCRETMLAVKFIAKYILKHTS
mmccpa 388 LLPESRIKPTCKETMLSVKFIAKYILKNTS
rtcpa2 388 LLPAKQILPTAEETWLGLKTIMEHVRDHPY
```

FIG. 5C

PLASMA CARBOXYPEPTIDASE

This is a continuation of co-pending application Ser. No. 07/959,944 filed on 14 Oct. 1992, now abandoned, which is a divisional of application Ser. No. 07/649,591, filed 1 Feb. 1991, now U.S. Pat. No. 5,201,161, granted Apr. 27, 1993.

FIELD OF THE INVENTION

This application relates to a carboxypeptidase that binds plasminogen. In particular, it relates to a plasma carboxypeptidase designated plasma carboxypeptidase B (PCPB) sharing some sequence identity with carboxypeptidase A and rat pancreas carboxypeptidase B that inhibits the enzymatic conversion by tissue plasminogen activator of plasminogen to plasmin in the presence of fibrinogen and does not inhibit plasmin activity.

BACKGROUND OF THE INVENTION

The carboxypeptidase family of exopeptidases constitute a diverse group of enzymes that hydrolyze carboxyl-terminal amide bonds in polypeptides. Carboxypeptidases from grains such as wheat and barley have been isolated and sequenced (Baulcombe et al., *J. Biol. Chem.*, 262: 13726-13735 [1987]; Svendsen and Breddam, *Carlsberg Res. Commun.*, 52: 285-295 [1987]), as well as carboxypeptidases from bacteria, and a carboxypeptidase Y has been isolated from yeast vacuoles and sequenced. Valls et al., *Cell*, 48: 887-897 [1987]; Svendsen et al., *Carlsberg Res. Commun.*, 47: 15-27 [1982]). The sequences of carboxypeptidase B from crayfish (Titani et al., *Biochemistry*, 23: 1245-1250 [1984]) and African lungfish (Reeck and Neurath, *Biochemistry*, 11: 3947-3955 [1972]) have been determined. A large number of mammalian tissues also produce these enzymes.

The exocrine pancreas synthesizes and secretes a subset of zinc metalloproteases. Two members of this metalloprotease family, carboxypeptidase A and carboxypeptidase B, have been purified from bovine pancreas and characterized. Barrett and MacDonald, *Mammalian Proteases, a Glossary and Bibliography*, Vol. 2 (Academic Press, London 1985), and references cited therein, including Titani et al., *Proc. Nat. Acad. Sci. USA*, 72: 1666-1670 [1975]; Bradshaw et al., *Biochemistry*, 10: 961-972 [1971]; Wade et al., *Biochimie*, 70: 1137-1142 [1988]. Bovine carboxypeptidase B was found to inhibit the activation of plasminogen by t-PA in the presence of degraded fibrin. Pannell et al., *J. Clin. Inv.*, 81: 853-859 (1988).

The bovine carboxypeptidases A and B have similar amino acid sequence, three-dimensional structure, and catalytic mechanisms, but differ in the substrate upon which they act. Carboxypeptidase A hydrolyzes carboxyl-terminal amide bonds in which the adjoining carboxy-terminal amino acid contains an aromatic or branched aliphatic side chain, whereas carboxypeptidase B prefers Lys or Arg residues as substrates at the carboxyl terminus.

Three carboxypeptidases differing in their substrate specificity (designated CPA1, CPA2, and CPB) were isolated from rat pancreas. Gardell et al., *J. Biol. Chem.*, 263: 17828-17836 (1988). The genes for rat CPA1 and CPA2 have been cloned and sequenced. Gardell et al., supra; Clauser et al., *J. Biol. Chem.*, 263: 17837-17845 (1988). See also Quinto et al., Proc. Natl. Acad. Sci. USA, 79: 31-35 (1982). Sequences have also been obtained of fragments from porcine carboxypeptidase A (Vendrell et al., *Biochem. Biophys. Res. Commun.*, 141:517-523 [1986]) and carboxypeptidase B (Aviles et al., *Biochem. Biophys. Res. Commun.*, 130:97-103 [1985]).

In addition to the pancreas, mast cells also contain large amounts of carboxypeptidase A, including rat and mouse peritoneal connective tissue mast cells [Everitt and Neurath, *FEBS Lett.*, 110: 292-296 (1980); Schwartz et al., *J. Immunol.*, 128: 1128-1133 (1982); Serafin et al., *J. Immunol.*, 139: 3771-3776 (1987)], mouse Kirsten sarcoma virus-immortalized mast cells [Reynolds et al., *J. Biol. Chem.*, 263: 12783-12791 (1988)], and human skin mast cells [Goldstein et al., *J. Immunol.*, 139: 2724-2729 (1987); Goldstein et al., *J. Clin. Invest.*, 83: 1630-1636 (1989)].

Mast cell carboxypeptidase A is a neutral to basically charged protein stored in the secretory granules of rat and mouse peritoneal connective tissue mast cells and mouse interleukin-3-dependent bone marrow-derived mast cells as a fully active enzyme bound ionically to acidically charged proteoglycans. Basically charged serine endopeptidases are similarly stored. The close approximation of carboxypeptidase A and serine protease activities within the protease-proteoglycan macromolecular complex is thought to facilitate sequential endopeptidase and exopeptidase cleavages of common protein substrates. Kokkonen and Kovanen, *J. Biol. Chem.*, 264: 10749-10755 (1989); Kokkonen et al., *J. Biol. Chem.*, 261: 16067-16072 (1986).

Mast cell carboxypeptidase A has been isolated from the secretorygranules of mouse peritoneal connective tissue mast cells and from a mouse Kirsten sarcoma virus-immortalized mast cell line, and a cDNA encoding this exopeptidase has been cloned. Reynolds et al., *J. Biol. Chem.*, 264: 20094-20099 (1989). In addition, the mast cell carboxypeptidase A from humans has been cloned and its sequence determined. Reynolds et al., *Proc. Natl. Acad. Sci. USA*, 86: 9480-9484 (1989).

Other mammalian carboxypeptidases besides carboxypeptidase B that specifically remove terminal basic amino acids include carboxypeptidase H (also known as enkephalin convertase or carboxypeptidase E), carboxypeptidase M, and carboxypeptidase N. The mammalian arginine/lysine carboxypeptidases have important functions in many biological processes, including protein digestion, activation, inactivation, or modulation of peptide hormone activity, and alteration of the physical properties of proteins and enzymes.

The actual role of these carboxypeptidases in vivo is likely related to their localization as well as their physical properties. For example, pancreatic carboxypeptidase B is not normally found outside the pancreas or small intestine except in the case of acute pancreatitis, consistent with its major function in protein degradation in the digestive tract. Delk et al., *Clin. Chem.*, 31: 1294-1300 (1985).

In contrast, human plasma carboxypeptidase N circulates in plasma as a large tetrameric complex of two active subunits (48-55 kD) and two glycosylated inactive subunits (83 kD) that stabilize the active subunits and keep them in the circulation. Carboxypeptidase N protects the body from potent vasoactive and inflammatory peptides containing COOH-terminal Arg or Lys released into the circulation. Erdos (ed.) in *Handbook of Experimental Pharmacology*, Vol. 25, Supplement, pp. 428-487, (Springer-Verlag, Heidelberg, 1979); Plummer and Hurwitz, *J. Biol. Chem.*, 253: 39-7-3912 (1978). Recently, carboxypeptidase N has been cloned and sequenced. Tan et al., *J. Biol. Chem.*, 265: 13-19 (1990); Gebhard et al., *Eur. J. Biochem.*, 178: 603-607 (1989); Skidgel et al., *Biochem. Biophys. Res. Commun.*, 154: 1323-1329 (1988).

Carboxypeptidase E (or H), an arginine/lysine carboxypeptidase with an acid pH optimum, is located in secretory granules of pancreatic islets, adrenal gland, pituitary, and brain. Zuhlke et al., *Ciba Found. Symp.*, 41: 183-195 (1975); Davidson and Hutton, *Biochem. J.*, 245: 575-582 (1987); Hook and Loh, *Proc. Natl. Acad. Sci. USA*, 81: 2776-2780 (1984). It is believed that this enzyme removes the residual COOH-terminal Arg or Lys remaining after initial endoprotease cleavage during prohormone processing at the intragranular acid pH. Fricker, *Annu. Rev. Physiol.*, 50: 309-321 (1988). Carboxypeptidase E has been isolated, cloned, and sequenced from different sources (rat: Frickler et al., *J. Mol. Endocrinol.*, 3: 666-673 [1989]; bovine: Fricker et al., *Nature*, 323: 461-464 [1986]; human: Hook and Affolter, *FEBS Lett.*, 238: 338-342 [1988]; Manser et al., *Biochem. J.*, 267: 517-525 [1990]).

Carboxypeptidase M is a membrane-bound arginine/lysine carboxypeptidase found in many tissues and cultured cells. Skidgel, *Trends pharmacol. Sci.*, 9: 299-304 (1988). Recently, it has been purified to homogeneity from human placenta. Skidgel et al., *J. Biol. Chem.*, 264: 2236-2241 (1989). Because of its presence on plasma membranes and optimal activity at neutral pH, it may act on peptide hormones at local tissue sites where it could control their activity before or after interaction with specific plasma membrane receptors. Sequencing has shown carboxypeptidase M to be a unique enzyme that exhibits some similarity to carboxypeptidases A, B, E, and N. Tan et al., *J. Biol. Chem.*, 264: 13165-13170 (1989).

It is an object of the present invention to identify a novel carboxypeptidase B isolated from plasma that shares some common structural features and catalytic and substrate binding sites with carboxypeptidase A and with pancreas carboxypeptidase B, and in its human embodiment shares the most sequence identity with known carboxypeptidases A and B.

It is another object to provide nucleic acid encoding such a polypeptide and to use this nucleic acid to produce the polypeptide in recombinant cell culture for diagnostic use or for potential therapeutic use in hemostatic regulation.

It is yet another object to provide derivatives and modified forms of such a new polypeptide, including amino acid sequence variants and covalent derivatives thereof.

It is an additional object to prepare immunogens for raising antibodies against such new polypeptide, as well as to obtain antibodies capable of binding it.

These and other objects of the invention will be apparent to the ordinary artisan upon consideration of the specification as a whole.

SUMMARY OF THE INVENTION

These objects are accomplished, in one aspect, by providing an isolated novel polypeptide that binds to plasminogen and is related structurally and functionally to carboxypeptidase A and pancreas carboxypeptidase B. This polypeptide is hereafter termed plasma carboxypeptidase B (PCPB), and includes N-terminal and C-terminal fragments thereof.

In another aspect, the invention provides a composition comprising the PCPB that is free of contaminating polypeptides of the animal species from which the PCPB is derived.

PCPB or fragments thereof (which also may be synthesized by in vitro methods) are fused (by recombinant expression or in vitro covalent methods) to an immunogenic polypeptide and this fusion polypeptide, in turn, is used to immunize an animal to raise antibodies against a PCPB epitope. Anti-PCPB is recovered from the serum of immunized animals. Alternatively, monoclonal antibodies are prepared from cells of the immunized animal in conventional fashion. Antibodies identified by routine screening will bind to PCPB but will not substantially cross-react with any other known carboxypeptidase, including carboxypeptidase A, pancreas carboxypeptidase B, or carboxypeptidases E, M, and N, or carboxypeptidases from non-mammalian sources.

Immobilized anti-PCPB antibodies are useful particularly in the diagnosis (in vitro or in vivo) or purification of PCPB, e.g., a mixture of PCPB is passed over a column to which the antibodies are bound.

Substitutional, deletional, or insertional variants of PCPB are prepared by in vitro or recombinant methods and screened for immuno-crossreactivity with PCPB and for PCPB antagonist or agonist activity.

PCPB also is derivatized in vitro to prepare immobilized PCPB and labeled PCPB, particularly for purposes of diagnosis of PCPB or its antibodies, or for affinity purification of PCPB antibodies.

PCPB, its derivatives, or its antibodies are formulated into physiologically acceptable vehicles, especially for therapeutic use. Such vehicles include sustained-release formulations of PCPB.

In further aspects, the invention provides a method for purifying PCPB comprising passing a mixture of PCPB over a plasminogen column, preferably eluted with epsilon-aminocaproic acid, or over a column to which PCPB antibodies are bound and recovering the fraction containing PCPB. Also provided is a method for coagulating blood comprising adding to the blood an effective amount of PCPB, wherein in one embodiment the method involves the in vivo treatment of a mammal (e.g., human) with a blood clotting disorder such as hemophilia.

In still other aspects, the invention provides an isolated nucleic acid molecule encoding PCPB, labeled or unlabeled, and a nucleic acid sequence that is complementary, or hybridizes under stringent conditions to, a nucleic acid sequence encoding PCPB, excluding nucleic acid sequences complementary to nucleic acid sequences encoding a carboxypeptidase A, a non-plasma, e.g., pancreas, carboxypeptidase B, a carboxypeptidase E, M, or N, or a non-mammalian carboxypeptidase, i.e., those known carboxypeptidases that are not PCPB.

In addition, the invention provides a replicable vector comprising the nucleic acid molecule encoding PCPB operably linked to control sequences recognized by a host transformed by the vector; host cells transformed with the vector; and a method of using a nucleic acid molecule encoding PCPB to effect the production of PCPB, comprising expressing the nucleic acid molecule in a culture of the transformed host cells and recovering PCPB from the host cell culture. The nucleic acid sequence is also useful in hybridization assays for PCPB nucleic acid.

In still further embodiments, the invention provides a method for producing PCPB comprising inserting into the DNA of a cell containing the nucleic acid molecule encoding PCPB a transcription modulatory element in sufficient proximity and orientation to the nucleic acid molecule to influence transcription thereof, with an optional further step comprising culturing the cell containing the transcription modulatory element and the nucleic acid molecule.

In still further embodiments, the invention provides a cell comprising the nucleic acid molecule encoding PCPB and an exogenous transcription modulatory element in sufficient proximity and orientation to the nucleic acid molecule to influence transcription thereof; and a host cell containing the nucleic acid molecule encoding PCPB operably linked to exogenous control sequences recognized by the host cell.

Still further is provided a method for obtaining cells having increased or decreased transcription of the nucleic acid molecule encoding PCPB comprising:

(a) providing cells containing the nucleic acid molecule;

(b) introducing into the cells a transcription modulating element; and (c) screening the cells for a cell in which the transcription of the nucleic acid molecule is increased or decreased.

BRIEF DESCRIPTION OF THE DRAWINGS

FIGS. 4A-4B depict the nucleotide sequence for the human PCPB gene and the deduced amino acid sequence. The arrow and positive numbers indicate where the mature sequence begins. A 46-mer sequence used to obtain full-length clones is also shown, as well as the potential clip site (arginine) for activation of PCPB as a carboxypeptidase, indicated by triple arrows. In addition, the expected residues involved in catalytic activity are in bold, and the expected residues involved in substrate binding are indicated by double underlining, with the expected residue that determines specificity of the PCPB as a carboxypeptidase B (Asp at 348) also indicated by italics.

FIGS. 5A-5C align the amino acid sequences among human PCPB (hpcpb), rat carboxypeptidase B (rcpb), rat carboxypeptidase A1 (rtcpa), human mast cell carboxypeptidase A (hmccpa), mouse mast cell carboxypeptidase A (mmccpa), and rat carboxypeptidase A2 (rtcpa2) to show the extent of sequence identity. The potential substrate binding site for the carboxypeptidases is indicated with an arrow.

DETAILED DESCRIPTION OF THE PREFERRED EMBODIMENTS

Figure 1:
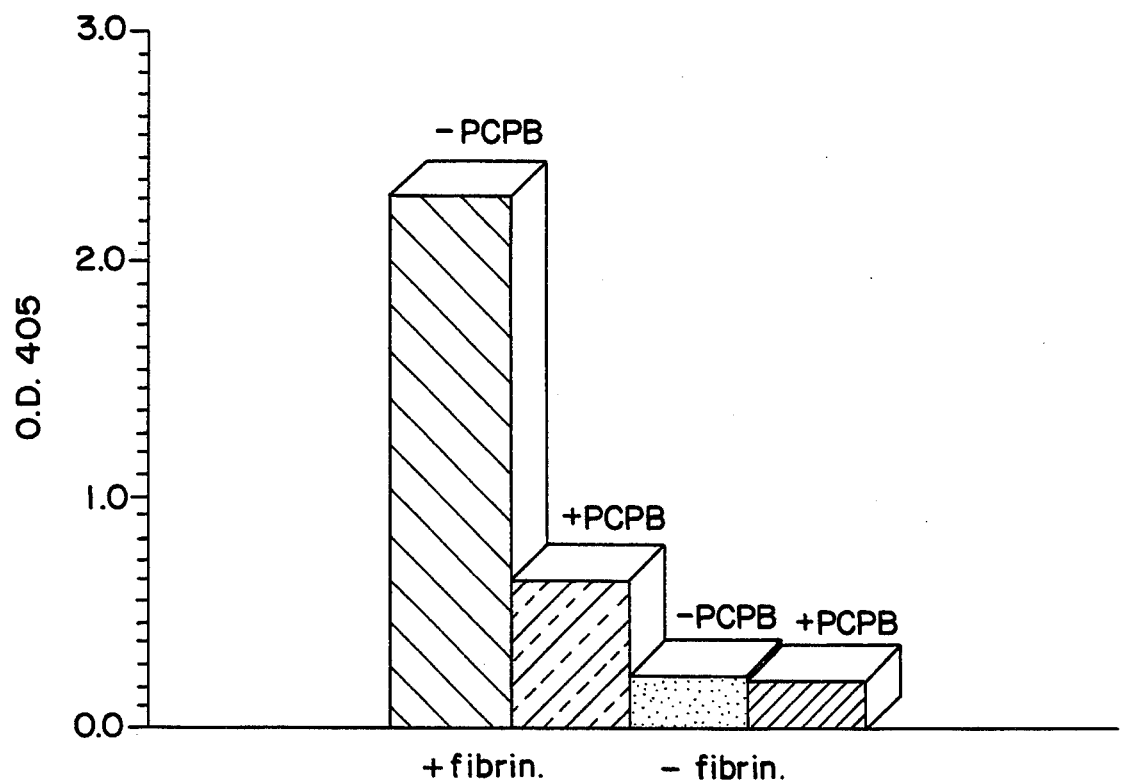
FIG. 1 illustrates a graph of optical density at 405 nm for mixtures of plasminogen and t-PA with and without PCPB and with and without fibrinogen ("fibrin.")
Figure 2:
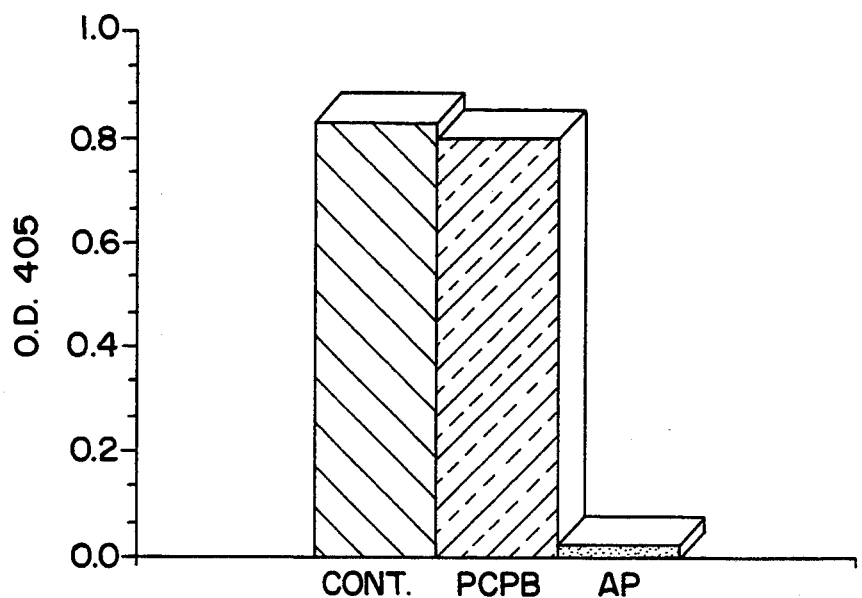
FIG. 2 illustrates a graph of optical density at 405 run for plasmin ("CONT."), plasmin plus PCPB ("PCPB"), and plasmin plus anti-plasmin ("AP")

In general, the following words or phrases have the indicated definition when used in the description, examples, and claims:

The expression "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

An "exogenous" element is defined herein to mean foreign to the cell, or homologous to the cell but in a position within the host cell in which the element is ordinarily not found.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included. Where distinct designations are intended, it will be clear from the context.

"Plasmids" are designated by a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the site for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 $\mu$g of plasmid or DNA fragment is used with about 1-2 units of enzyme in about 20 $\mu$l of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein or polypeptide is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (Maniatis et al., *Molecular Cloning: A Laboratory Manual* [New York: Cold Spring Harbor Laboratory, 1982]pp. 133-134).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawnet al., *Nucleic Acids Res.*, 9:6103–6114 (1981), and Goeddel et al., Nucleic Acids Res. 8: 4057 (1980).

"Southern analysis" is a method by which the presence of DNA sequences in a digest or DNA-containing composition is confirmed by hybridization to a known, labeled oligonucleotide or DNA fragment. For the purposes herein, unless otherwise provided, Southern analysis shall mean separation of digests on 1 percent agarose, denaturation, and transfer to nitrocellulose by the method of Southern, *J. Mol. Biol.*, 98: 503–517 (1975), and hybridization as described by Maniatis et al., Cell 15: 687–701 (1978).

"Ligation" refers to the process of forming phosphodiester bonds between two double-stranded nucleic acid fragments (Maniatis et al., 1982, supra, p. 146). Unless otherwise provided, ligation may be accomplished using known buffers and conditions with 10 units of T4 DNA ligase ("ligase") per 0.5 μg of approximately equimolar amounts of the DNA fragments to be ligated.

"Preparation" of DNA from transformants means isolating plasmid DNA from microbial culture. Unless otherwise provided, the alkaline/SDS method of Maniatis et al., 1982, supra, p. 90, may be used.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP 266,032 published 4 May 1988, or via deoxynucleoside H-phosphonate intermediates as described by Froehler et al., *Nucl. Acids Res.*, 14: 5399–5407 [1986]). They are then purified on polyacrylamide gels.

The technique of "polymerase chain reaction," or "PCR," as used herein generally refers to a procedure wherein minute amounts of a specific piece of DNA are amplified as described in U.S. Pat. No. 4,683,195 issued 28 Jul. 1987. Generally, sequence information from the ends of the stretch of interest or beyond needs to be available, such that oligonucleotide primers can be designed; these primers will point towards one another, and will be identical or similar in sequence to opposite strands of the template to be amplified. The 5' terminal nucleotides of the two primers will coincide with the ends of the amplified material. PCR can be used to amplify specific DNA sequences from total genomic DNA, cDNA transcribed from total cellular RNA, bacteriophage or plasmid sequences, etc. See generally Mullis et al., *Cold Spring Harbor Symp. Quant. Biol.*, 51: 263 (1987); Erlich, ed., *PCR Technology*, (Stockton Press, N.Y., 1989).

"PCPB" is defined to be a polypeptide or protein encoded by the human PCPB nucleotide sequence set forth in FIG. 4; a polypeptide that is the translated amino acid sequence set forth in FIG. 4; a polypeptide that is the translated mature amino acid sequence shown in FIG. 4; fragments thereof having greater than about 5 residues comprising an immune epitope or other biologically active site of PCPB (such as the N-terminal activation peptide fragment from +1 to +92 of the FIG. 4 sequence numbered starting at the mature N-terminal phenylalanine residue, and the C-terminal carboxypeptidase-active fragment from +93 to +401 of the FIG. 4 amino acid sequence); amino acid sequence variants of said FIG. 4 sequence wherein an amino acid residue has been inserted N- or C-terminal to, or within, said FIG. 4 sequence or its fragment as defined above; and/or amino acid sequence variants of said FIG. 4 sequence or its fragment as defined above wherein an amino acid residue of said FIG. 4 sequence or fragment thereof has been substituted by another residue, including predetermined mutations by, e.g., site-directed or PCR mutagenesis, and other animal species of PCPB such as rat, porcine, non-human primate, equine, murine, and ovine preproPCPB, and alleles and other naturally occurring variants of the foregoing and human sequences; and derivatives of PCPB or its fragments as defined above wherein the PCPB or its fragments have been covalently modified by substitution with a moiety other than a naturally occurring amino acid. Such fragments and variants exclude any polypeptide heretofore identified, including any known carboxypeptidase of any animal species or any known fragment of such carboxypeptidase, including plasma, mast cell, or pancreas carboxypeptidase A, pancreas carboxypeptidase B, and carboxypeptidases E, M, and N, and non-mammalian carboxypeptidases such as plant, insect, fish, yeast, and bacterial carboxypeptidases. PCPB amino acid sequence variants generally will share at least about 75% (preferably >80%, more preferably >85%) sequence identity with the translated sequence shown in FIG. 4, after aligning (introducing any necessary spaces) to provide maximum homology and not considering any conservative substitutions as part of the sequence identity. Neither N-nor C-terminal extensions nor insertions shall be construed as reducing homology.

The PCPB herein is capable of immunologically crossreacting with a polyclonal antibody raised to native PCPB and/or is positive in one of the following two bioassays: it has no effect on plasmin activity in an assay using the chromogenic plasmin substrate S-2251 assay as described in the examples; and/or it blocks conversion of plasminogen to plasmin in the presence of fibrinogen fragments and tissue plasminogen activator using the S-2251 assay where a 1:1 molar ratio of candidate polypeptide to plasminogen is employed.

The preferred PCPB is human PCPB, which more preferably has a molecular weight on non-reducing SDS-PAGE of about 60 kD and has in its mature form the N-terminal sequence PheGlnSer.

In one embodiment, PCPB is purified from human plasma (preferably an ammonium sulfate precipitated fraction from plasma) or from transformed cell culture (lysed cells or supernatant) by passing a mixture of the PCPB over a column to which plasminogen is bound, such as a controlled glass pore column, and recovering the fraction containing the PCPB by elution and washing with appropriate solvent(s). Preferably the column is eluted with epsilon-aminocaproic acid (EACA), and more preferably the column is eluted with 0.2M EACA or a gradient of 0 to 50 mM EACA. If the PCPB is being purified from a native source, after the plasminogen column treatment, the PCPB fraction is preferably passed over a column to which protein-A is bound to remove any contaminating immunoglobulins, and the fraction containing PCPB is recovered. The thus-recovered fraction is then preferably passed over another column to which plasminogen is bound using a 0 to 50 mM gradient of EACA, and the PCPB-containing fraction is recovered.

"Isolated" PCPB is PCPB that is identified and separated from contaminant polypeptides in the animal or human source of the PCPB.

Amino acid sequence variants of PCPB are prepared by introducing appropriate nucleotide changes into the PCPB DNA, or by in vitro synthesis of the desired PCPB. Such variants include, for example, deletions from, or insertions or substitutions of, residues within the amino acid sequence shown for human PCPB in FIG. 4. Any combination of deletion, insertion, and substitution is made to arrive at the final construct, provided that the final construct possesses the desired characteristics. The amino acid changes also may result in further modifications of PCPB upon expression in recombinant hosts, e.g. introducing or moving sites of glycosylation, or introducing membrane anchor sequences (in accordance with PCT WO 89/01041 published 9 Feb. 1989).

There are two principal variables in the construction of amino acid sequence variants: the location of the mutation site and the nature of the mutation. These are variants from the FIG. 4 sequence, and may represent naturally occurring alleles (which will not require manipulation of the PCPB DNA) or predetermined mutant forms made by mutating the DNA, either to arrive at an allele or a variant not found in nature. In general, the location and nature of the mutation chosen will depend upon the PCPB characteristic to be modified.

For example, candidate PCPB antagonists (suitable as adjuncts to thrombolytic therapy such as t-PA) or super agonists will be initially selected by locating sites that are identical or highly conserved among PCPB and known carboxypeptidases, especially among carboxypeptidases A, B and N. These sites then will be modified in series, e.g., by (1) substituting first with conservative choices and then with more radical selections depending upon the results achieved, (2) deleting the target residue, or (3) inserting residues of the same or a different class adjacent to the located site, or combinations of options 1–3.

One helpful technique is called "alanine scanning mutagenesis." Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. cunningham and Wells, Science, 244: 1081–1085 (1989). Those domains demonstrating functional sensitivity to the substitutions then are refined by introducing further or other variants at or for the sites of substitution.

Obviously, such variations that, for example, convert PCPB into a known carboxypeptidase such as plasma, pancreas, or mast cell carboxypeptidase A, pancreas carboxypeptidase B, plasma carboxypeptidase N, carboxypeptidases E or M, or non-mammalian carboxypeptidases are not included within the scope of this invention, nor are any other PCPB variants or polypeptide sequences that are not novel and unobvious over the prior art. Thus, while the site for introducing an amino acid sequence variation is predetermined, the nature of the mutation per se need not be predetermined. For example, to optimize the performance of a mutation at a given site, ala scanning or random mutagenesis is conducted at the target codon or region and the expressed PCPB variants are screened for the optimal combination of desired activity.

Amino acid sequence deletions generally range from about 1 to 30 residues, more preferably about 1 to 10 residues, and typically are contiguous. Contiguous deletions ordinarily are made in even numbers of residues, but single or odd numbers of deletions are within the scope hereof. Deletions may be introduced into regions of low homology among PCPB and carboxypeptidases A and B (which share the most sequence identity to the human PCPB amino acid sequence) to modify the activity of PCPB. Deletions from PCPB in areas of substantial homology with carboxypeptidases A and B will be more likely to modify the biological activity of PCPB more significantly. The number of consecutive deletions will be selected so as to preserve the tertiary structure of PCPB in the affected domain, e.g., beta-pleated sheet or alpha helix.

Amino acid sequence insertions include amino- and/or carboxyl-terminal fusions ranging in length from one residue to polypeptides containing a hundred or more residues, as well as intrasequence insertions of single or multiple amino acid residues. Intrasequence insertions (i.e., insertions within the mature PCPB sequence) may range generally from about 1 to 10 residues, more preferably 1 to 5, most preferably 1 to 3. Insertions are preferably made in even numbers of residues, but this is not required. Examples of terminal insertions include mature PCPB with an N-terminal methionyl residue, an artifact of the direct expression of mature PCPB in recombinant cell culture, and fusion of a heterologous N-terminal signal sequence to the N-terminus of the mature PCPB molecule to facilitate the secretion of mature PCPB from recombinant hosts. Such signals generally will be homologous to the intended host cell and include STII or lpp for *E. coli*, alpha factor for yeast, and vital signals such as herpes gD for mammalian cells. Other insertions include the fusion to the N- or C-terminus of PCPB of immunogenic polypeptides, e.g., bacterial polypeptides such as beta-lactamase or an enzyme encoded by the *E. coli* trp locus, or yeast protein, and C-terminal fusions with proteins having a long half-life such as immunoglobulin constant regions, albumin, or ferritin, as described in WO 89/02922 published 6 Apr. 1989.

The third group of variants are those in which at least one amino acid residue in the PCPB molecule, and preferably only one, has been removed and a different residue inserted in its place. The sites of greatest interest for substitutional mutagenesis include sites where the amino acids found in known carboxypeptidases A and/or B and novel PCPB are substantially different in terms of side-chain bulk, charge, or hydrophobicity, but where there also is a high degree of sequence identity at the selected site within various animal analogues of carboxypeptidase A or carboxypeptidase B (e.g., among all the animal carboxypeptidase A molecules or among all the animal carboxypeptidase B molecules). This analysis will highlight residues that may be involved in the differentiation of activity of the carboxypeptidases, and therefore, variants at these sites may affect such activities.

Other sites of interest are those in which the residues are identical among all animal species of PCPB and carboxypeptidase A or non-plasma derived carboxypeptidase B, this degree of conformation suggesting importance in achieving biological activity common to these enzymes. These sites, especially those falling within a sequence of at least three other identically conserved sites, are substituted in a relatively conservative manner. Such conservative substitutions are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Trypsin or other protease cleavage sites are identified by inspection of the encoded amino acid sequence for an arginyl or lysinyl residue. These are rendered inactive to protease by substituting the residue with another residue, preferably a basic residue such as glutamine or a hydrophobic residue such as serine; by deleting the residue; or by inserting a prolyl residue immediately after the residue.

In another embodiment, any methionyl residues other than the starting methionyl residue of the signal sequence, or any residue located within about three residues N- or C-terminal to each such methionyl residue, is substituted by another residue (preferably in accord with Table 1) or deleted. Alternatively, about 1–3 residues are inserted adjacent to such sites.

Sites particularly suited for conservative substitutions include, numbered from the N-terminus of the mature PCPB, P135, L136, Y137, V138, L139, K140, A151, I152, W153, I154, D155, G157, I158, A160, W163, I164, S165, P166, A167, F168, N202, V203, D204, G205, Y206, Y208, S209, W210, K211, K212, N213, R214, M215, W216, R217, K218, N219, R220, I229, G230, T231, D232, L233, N234, R235, N236, F237, P261, E262, E264, E266, V267, K268, A269, V270, I281, K282, A283, Y284, I285, H288, Y290, Q292, Y352, D353, L354, G355, I356, K357, Y358, F360, T361, E363, L364, R365, D366, T367, G368, G371, L373, L374, P375, E376, I379, K380, P381, T382, R384, and E385.

Figure 5A:
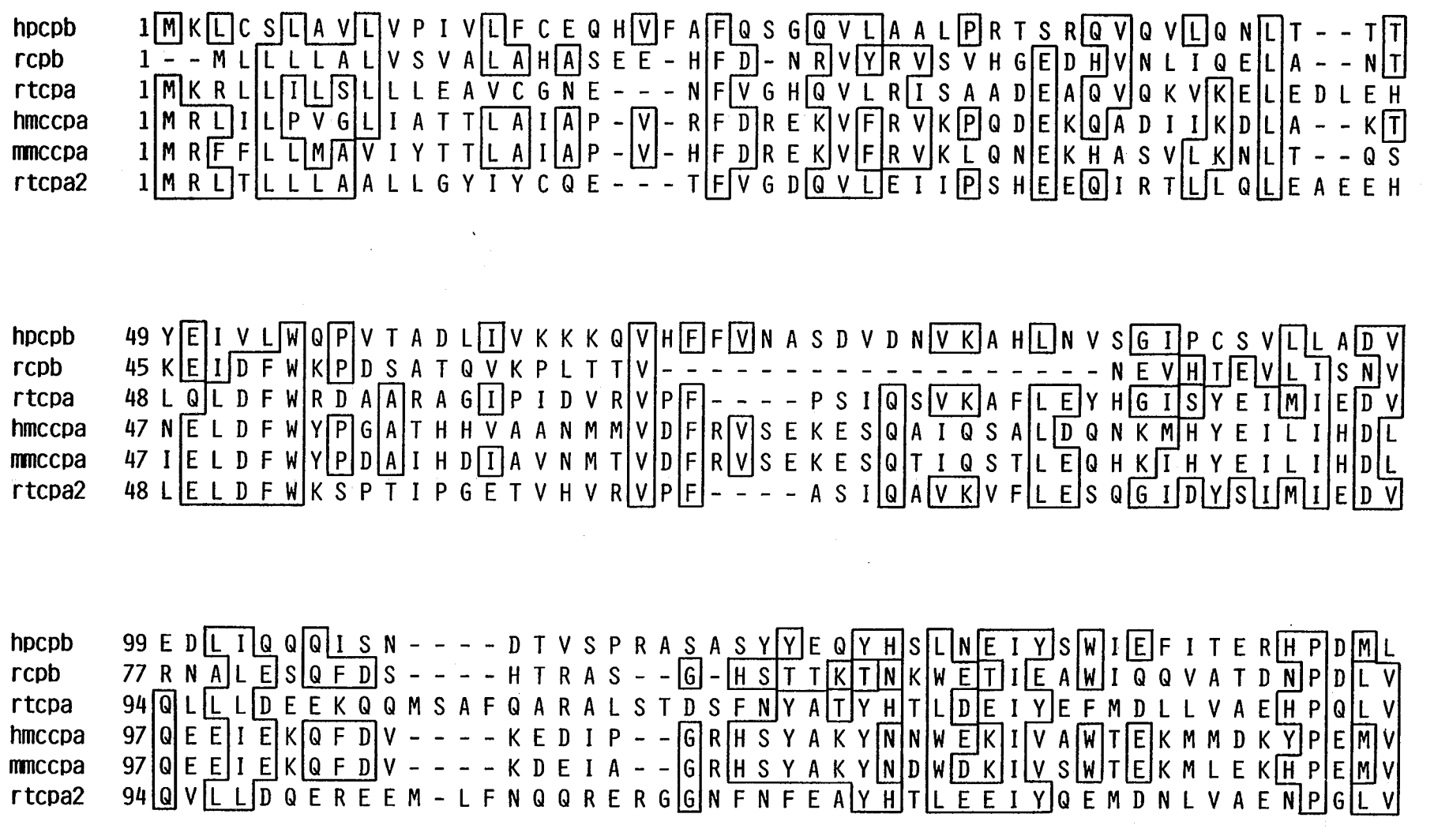
Figure 5B:
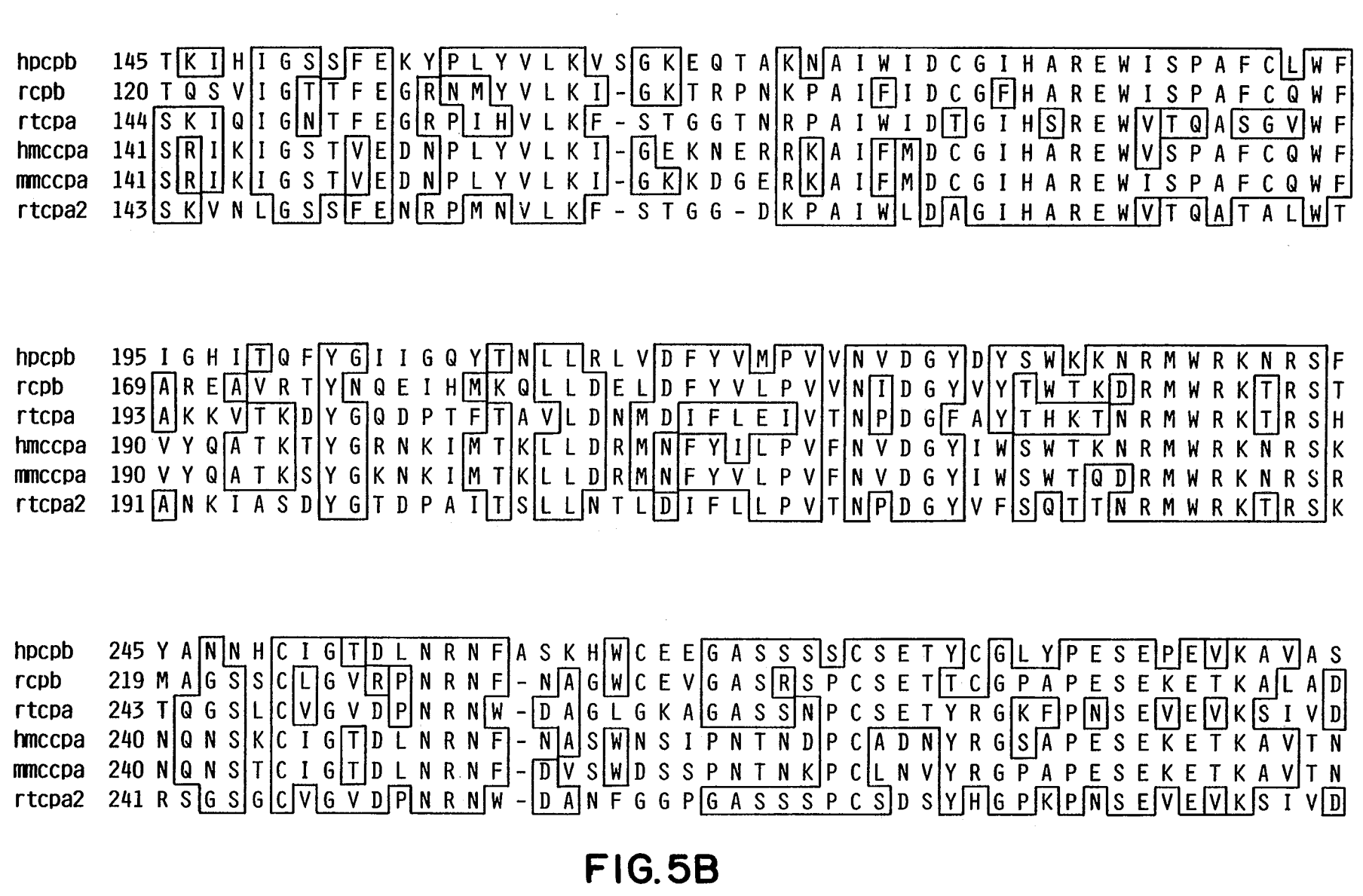

It is noted that the histidine residues at positions 159 and 288, the glutamic acid at position 162, and the glycine at position 347, all of which except the glycine are conserved among the carboxypeptidases depicted in FIG. 5, are catalytic sites that are preferably not altered, e.g., by substitution or deletion. Also, the arginine residue at position 161, the asparagine residue at position 234, the arginine residue at position 235, the tyrosine residue at position 290, the aspartic acid residues at positions 348 and 349, and the phenylalanine residue at position 372 are substrate binding sites that are not generally altered as by substitution with another amino acid or by deletion, particularly the aspartic acid at position 348, which is believed to determine substrate specificity of PCPB as a carboxypeptidase B (see FIG. 5).

Any cysteine residues not involved in maintaining the proper conformation of PCPB also may be substituted, generally with serine, to improve the oxidative stability of the molecule and prevent aberrant crosslinking. Sites other than those set forth in this paragraph are suitable for deletional or insertional studies generally described above.

Substantial modifications in function or immunological identity are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side chain properties:

(1) hydrophobic: norleucine, met, ala, val, leu, ile;
(2) neutral hydrophilic: cys, set, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another. Such substituted residues also may be introduced into the conservative substitution sites set forth above or, more preferably, into the remaining (non-conserved) sites.

Examples of PCPB variants include PCPB(150NAI152-->NAS or NAT) (this adds an N-linked glycosylation site); PCPB(R11-Q83); PCPB(G4-C69) (variants so depicted are fragments containing the residues indicated); PCPB(G4-K59); PCPB(C69-C156); PCPB(C69-C169); PCPB(C69-C228); PCPB(C69-C243); PCPB(C69-C252); PCPB(R12-R92); PCPB(R12-R117); PCPB(R92-R117); PCPB(C156-C169); PCPB(C169-C228); PCPB(C169-C243); PCPB(C169-C252); PCPB(C169-C257); PCPB(C169-C383); PCPB(C69-C257); PCPB(C69-C383); PCPB(R12-C156); PCPB(R92-R384); PCPB(R92-R275); PCPB(R92-R330); PCPB(K44-K124); PCPB(R12-K124); PCPB(R12-K44); PCPB(K124-K282); PCPB(G4-C69) E I L I H D V E D L; PCPB(G4-Q83) F D V K E; PCPB(R11-Q83) F D S M T; PCPB(R92-R399) H T S; PCPB(R92-R399) H L Y; PCPB(R92-R384) E T M L A V K; PCPB(R92-K392) I A K Y I L K H T S; PCPB(R92-K392) I A N Y V R E H L Y; PCPB(ΔC69); PCPB(ΔC156); PCPB(ΔC169-ΔC383) (variants depicted in this fashion comprise deletions of the indicated span of residues, inclusive); W153→F; I154→M; I158→F; I164→V; L170→Q; V201→F or T; D207→I or V; Y208→W; K211→T; N225→G; I229→L or V; T231→V; L233→P; P265→K or V; V267→T; S272→D; L274→I; L354→Q; Y358→H; S359→T; T369→K or F; Y370→F or R; R377→S; and Y378→R or Q. Covalent modifications of PCPB molecules are included within the scope of this invention. Variant PCPB fragments having up to about 40 residues may be conveniently prepared by in vitro synthesis. In addition, covalent modifications are introduced into the molecule by reacting targeted amino acid residues of the PCPB with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable methods for derivatizing α-amino-containing residues include use of imidoesters such as methyl picolinimidate; pyridoxal phosphate; pyridoxal; chloroborohydride; trinitrobenzenesulfonic acid; O-methylisourea; and 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'-N=C=N-R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking PCPB to a water-insoluble support matrix or surface for use in the method for purifying anti-PCPB antibodies, and vice versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. No. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W. H. Freeman & Co., San Francisco, ppl. 79–86 [1983]), acetylation of the N-terminal amine, and amidation of any C-terminal carboxyl group. PCPB also is covalently linked to nonproteinaceous polymers, e.g. polyethylene glycol, polypropylene glycol or polyoxyalkylenes, in the manner set forth in U.S. Pat. No. 4,640,835; 4,496,689; 4,301,144; 4,670,427; 4,791,192 or 4,179,337.

PCPB "nucleic acid" is defined as RNA or DNA that encodes a PCPB, is complementary to nucleic acid sequence encoding PCPB, hybridizes to such nucleic acid and remains stably bound to it under stringent conditions, or encodes a polypeptide sharing at least 75% sequence identity, preferably at least 80%, and more preferably at least 85%, with the translated amino acid sequence shown in FIG. 4. It is typically at least about 10 bases in length and preferably has PCPB biological or immunological activity, including the nucleic acid encoding an activation peptide fragment having the nucleotide sequence shown in FIG. 4 beginning at the codon for phenylalanine at the mature N-terminus and ending at the codon for arginine at position 92, and the nucleic acid encoding a carboxypeptidase-active fragment having the nucleotide sequence shown in FIG. 4 beginning at the codon for alanine at position 93 and ending at the codon for the valine at position 401. Such hybridizing or complementary nucleic acid, however, is defined further as being novel and unobvious over any prior art nucleic acid including that which encodes, hybridizes under stringent conditions, or is complementary to nucleic acid encoding a known carboxypeptidase, including plasma, pancreas, and mast cell carboxypeptidase A, non-plasma derived carboxypeptidase B, carboxypeptidases E, M, or N, and a non-mammalian carboxypeptidase.

"Stringent conditions" are those that (1) employ low ionic strength and high temperature for washing, for example, 0,015M NaCl/0.0015M sodium titrate/0.1% $NaDodSO_4$ at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaC1, 75 mM sodium citrate at 42° C. Another example is use of 50% formamide, 5×SSC (0.75M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS.

DNA encoding PCPB is obtained from a liver cDNA library, or genomic DNA, or by in vitro synthesis. Hybridizing nucleic acid generally is obtained by in vitro synthesis. Identification of PCPB DNA most conveniently is accomplished by probing human cDNA or genomic libraries by labeled oligonucleotide sequences selected from the FIG. 4 sequence in accord with known criteria, among which is that the sequence should be of sufficient length and sufficiently unambiguous that false positives are minimized. Typically, a $^{32}$P-labeled oligonucleotide having about 30 to 50 bases is sufficient, particularly if the oligonucleotide contains one or more codons for methionine or tryptophan. "Isolated" nucleic acid will be nucleic acid that is identified and separated from contaminant nucleic acid encoding other polypeptides from the source of nucleic acid. The nucleic acid may be labeled for diagnostic and probe purposes, using a label as described and defined further below in the discussion of diagnostic assays.

Of particular interest is PCPB nucleic acid that encodes a full-length molecule, including but not necessarily the native signal sequence thereof. Nucleic acid encoding full-length protein is obtained by screening selected cDNA (not kidney) or genomic libraries using the deduced amino acid sequence disclosed herein for the first time, and, if necessary, using conventional primer extension procedures to secure DNA that is complete at its 5' coding end. Such a clone is readily identified by the presence of a start codon in reading frame with the original sequence.

DNA encoding amino acid sequence variants of PCPB is prepared by a variety of methods known in the art. These methods include, but are not limited to, isolation from a natural source (in the case of naturally occuring amino acid sequence variants) or preparation by oligonucleotide-mediated (or site-directed) mutagenesis, PCR mutagenesis, and cassette mutagenesis of an earlier prepared variant or a non-variant version of PCPB.

Oligonucleotide-mediated mutagenesis is a preferred method for preparing substitution, deletion, and insertion variants of PCPB DNA. This technique is well known in the art as described by Adelman et al., DNA, 2: 183 (1983). Briefly, PCPB DNA is altered by hybridizing an oligonucleotide encoding the desired mutation to a DNA template, where the template is the single-stranded form of the plasmid containing the unaltered or native DNA sequence of PCPB. After hybridization, a DNA polymerase is used to synthesize an entire second complementary strand of the template that will thus incorporate the oligonucleotide primer, and will code for the selected alteration in the PCPB DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. USA*, 75: 5765 (1978).

The DNA template can only be generated by those vectors that are either derived from bacteriophage M13 vectors (the commercially available M13 mp18 and M13 mp19 vectors are suitable), or those vectors that contain a single-stranded phage origin of replication as described by Viera et al. *Meth. Enzymol.*, 153: 3 (1987).

Thus, the DNA that is to be mutated must be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, N.Y. 1989).

For alteration of the native DNA sequence, the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of PCPB, and the other strand (the original template) encodes the native, unaltered sequence of PCPB. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

Mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid variants of PCPB. This technique refers to the following procedure (see Erlich, supra, the chapter by R. Higuchi, p. 61–70): When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

In a specific example of PCR mutagenesis, template plasmid DNA (1 µg) is linearized by digestion with a restriction endonuclease that has a unique recognition site in the plasmid DNA outside of the region to be amplified. Of this material, 1–5 ng is added to a PCR mixture containing 16.6 mM $(NH_4)_2SO_4$, 67 mM Tris.HCl (pH 8.8), 6.7 mM $MgCl_2$, 6.7 µM EDTA, 10 mM 2-mercaptoethanol, 1 mM each dATP, dCTP, dGTP, and TTP, 170 µg/ml bovine serum albumin, 25 pmole of each oligonucleotide primer, and 1 µl *Thermus aquaticus* (Taq) DNA polymerase (5 units/µl, purchased from Perkin-Elmer Cetus, Norwalk, Conn. and Emeryville, Calif.) in a final volume of 50 µl in a 0.5-ml reaction vial. The reaction mixture is overlayed with 35 µl mineral oil and inserted into a DNA Thermal Cycler (purchased from Perkin-Elmer Cetus) programmed as follows:

| | |
|---|---|
| time-delay file | 12 min. 94° C. |
| thermo-cycle file | 1 min. 50° C. |
| | 2–3 min. 68–72° C. |
| | 1 min. 94° C. |
| | 20 cycles |
| time-delay file | 4 min. 50° C. |
| time-delay file | 12 min. 68° C. |
| soak file | 4° C. |

Each file shown above is linked to the one on the next line. At the end of the program, the reaction vial is removed from the thermal cycler and the aqueous phase transferred to a new vial, extracted with phenol/chloroform/isoamylalcohol (50:50:1 vol), and ethanol precipitated, and the DNA is recovered by standard procedures. This material is subsequently subjected to the appropriate treatments for insertion into a vector.

Another method for preparing variants, cassette mutagenesis, is based on the technique described by Wells et al., *Gene*, 34: 315 (1985). The starting material is the plasmid (or other vector) comprising the PCPB DNA to be mutated. The codon(s) in the PCPB DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the PCPB DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3′ and 5′ ends that are compatible with the ends of the linearized plasmid, such that it can be directly ligated to the plasmid. This plasmid now contains the mutated PCPB DNA sequence.

The PCPB-encoding nucleic acid, whether variant or cDNA or genomic DNA, is ligated into a replicable vector for further cloning or for expression. Vectors are useful for performing two functions in collaboration with compatible host cells (a host-vector system). One function is to facilitate the cloning of the nucleic acid that encodes the PCPB, i.e., to produce usable quantities of the nucleic acid. The other function is to direct the expression of PCPB. One or both of these functions are performed by the vector-host system. The vectors will contain different components depending upon the function they are to perform as well as the host cell that is selected for cloning or expression.

Particularly useful in the invention are expression vectors that provide for the transient expression in mammalian cells of DNA encoding PCPB. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17–16.22. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of PCPB that have carboxypeptidase or other PCPB-like activity.

Each expression vector will contain nucleic acid that encodes PCPB as described above. The PCPBs of this invention are expressed directly in recombinant cell culture as an N-terminal methionyl analogue, or as a fusion with a heterologous polypeptide, preferably a signal sequence or other polypeptide having a specific cleavage site at the N-terminus of the mature protein or polypeptide. For example, in constructing a prokaryotic secretory expression vector for PCPB, the native PCPB signal is employed with hosts that recognize that signal. When the secretory leader is "recognized" by the host, the host signal peptidase is capable of cleaving a fusion of the leader polypeptide fused at its C-terminus to the desired mature PCPB.

For host prokaryotes that do not process the PCPB signal, the signal is substituted by a prokaryotic signal selected, for example, from the group of the alkaline phosphatase, penicillinase, lpp, or heat-stable enterotoxin II leaders. For yeast secretion the native signal may be substituted by the yeast invertase, alpha factor, or acid phosphatase leaders. In mammalian cell expression the native signal (i.e., the PCPB presequence that normally directs secretion of PCPB from human cells in vivo) is satisfactory, although other mammalian secretory protein signals are suitable such as signals from other animal PCPBs, signals from a carboxypeptidase A, E, M, or N or non-plasma derived carboxypeptidase B, and signals from secreted polypeptides of the same or related species, as are viral secretory leaders, for example, the herpes simplex gD signal.

If the signal sequence is from another carboxypeptidase molecule, it may be the precursor sequence spanning from the initiating methionine (M) residue shown in FIG. 5 of a carboxypeptidase A or B up to the alanine (A) residue just before the first amino acid of the mature protein, or a consensus or combination sequence from any two or more of the precursors of different carboxypeptidases taking into account homologous regions of the precursors. The DNA for such precursor region is ligated in reading frame to DNA encoding the mature PCPB.

Expression and cloning vectors contain a nucleic acid sequence that enables the vector to replicate in one or more selected host cells. Generally, in cloning vectors this sequence is one that enables the vector to replicate independently of the host chromosomes, and includes origins of replication or autonomously replicating sequences. Such sequences are well known for a variety of bacteria, yeast, and viruses. The origin of replication from the plasmid pBR322 is suitable for most Gram-negative bacteria, the 2$\mu$ plasmid origin is suitable for yeast, and various viral origins (SV40, polyoma, adenovirus, VSV or BPV) are useful for cloning vectors in mammalian cells. Origins are not needed for mammalian expression vectors (the SV40 origin may typically be used only because it contains the early promoter). Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA also is cloned by insertion into the host genome. This is readily accomplished with Bacillus species, for example, by including in the vector a DNA sequence that is complementary to a sequence found in Bacillus genomic DNA. Transfection of Bacillus with this vector results in homologous recombination with the genome and insertion of PCPB DNA. However, the recovery of genomic DNA encoding PCPB is more complex than that of an exogenously replicated vector because restriction enzyme digestion is required to excise the PCPB DNA.

Expression and cloning vectors should contain a selection gene, also termed a selectable marker. This is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate, or tetracycline, (b) complement auxotrophic deficiencies, or (c) supply critical nutrients not available from complex media, e.g. the gene encoding D-alanine racemase for Bacilli.

A suitable selection gene for use in yeast is the trpl gene present in the yeast plasmid YRp7 (Stinchcomb et al., *Nature,* 282: 39 [1979]; Kingsman et al., Gene, 7: 141 1979]; or Tschemper et al., Gene, 10: 157 [1980]). The trpl gene provides a selection marker for a mutant strain of yeast lacking the ability to grow in tryptophan, for example, ATCC No. 44076 or PEP4-1 (Jones, *Genetics,* 85: 12 1977]). The presence of the trpl lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et al., *J, Molec. Appl. Genet.,* 1: 327 [1982]), mycophenolic acid (Mulligan et al., *Science,* 209: 1422 [1980]) or hygromycin (Sugden et al., *Mol. Cell. Biol.,* 5: 410–413 [1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the PCPB nucleic acid, such as dihydrofolate reductase (DHFR) or thymidine kinase. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes PCPB. Amplification is the process by which genes in greater demand for the production of a protein critical for growth are reiterated in tandem within the chromosomes of successive generations of recombinant cells. Increased quantities of PCPB are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, Proc. Natl. Acad. Sci. USA, 77: 4216 [1980]. The transformed cells are then exposed to increased levels of methotrexate. This leads to the synthesis of multiple copies of the DHFR gene, and, concomitantly, multiple copies of other DNA comprising the expression vectors, such as the DNA encoding PCPB. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060). Alternatively, host cells [particularly wild-type hosts that contain endogenous DHFR] transformed or co-transformed with DNA sequences encoding PCPB, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

Other methods, vectors, and host cells suitable for adaptation to the synthesis of PCPB in recombinant vertebrate cell culture are described in Gething et al., Nature, 293: 620-625 [1981]; Mantei et al., Nature, 281: 40-46 [1979]; Levinson et al.; EP 117,060; and EP 117,058. A particularly useful plasmid for mammalian cell culture expression of PCPB is pRK5 (EP pub. no. 307,247) or pSVI6B (U.S. Ser. No. 07/441,574 filed 22 Nov. 1989, the disclosure of which is incorporated herein by reference).

Expression vectors, unlike cloning vectors, should contain a promoter that is recognized by the host organism and is operably linked to the PCPB nucleic acid. Promoters are untranslated sequences located upstream from the start codon of a structural gene (generally within about 100 to 1000 bp) that control the transcription and translation of nucleic acid under their control. They typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to PCPB-encoding DNA by removing them from their gene of origin by restriction enzyme digestion, followed by insertion 5' to the start codon for PCPB. This is not to say that the genomic PCPB promoter is not usable. However, heterologous promoters generally will result in greater transcription and higher yields of expressed PCPB.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. Linking is accomplished by ligation at convenient restriction sites. If such sites do not exist, then synthetic oligonucleotide adaptors or linkers are used in accord with conventional practice.

Promoters suitable for use with prokaryotic hosts include the β-lactamase and lactose promoter systems (Chang et al., Nature, 275: 615 [1978]; and Goeddel et al., Nature, 281: 544 [1979]), alkaline phosphatase, a tryptophan (trp) promoter system (Goeddel, Nucleic Acids Res., 8: 4057 [1980] and EP 36,776) and hybrid promoters such as the tac promoter (deBoer et al., Proc, Natl. Acad. Sci. USA, 80: 21-25 1983]). However, other known bacterial promoters are suitable. Their nucleotide sequences have been published, thereby enabling a skilled worker operably to ligate them to DNA encoding PCPB (Siebenlist et al., Cell, 20: 269 [1980]) using linkers or adaptors to supply any required restriction sites. Promoters for use in bacterial systems also will contain a Shine-Dalgarno (S.D.) sequence operably linked to the DNA encoding PCPB.

Suitable promoting sequences for use with yeast hosts include the promoters for 3-phosphoglycerate kinase (Hitzeman et al., J. Biol. Chem., 255: 2073 [1980]) or other glycolytic enzymes (Hess et al., J. Adv. Enzyme Reg., 7: 149 [1968]; and Holland, Biochemistry, 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Expression control sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into mammalian expression vectors.

PCPB transcription from vectors in mammalian host cells is controlled by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, from heat-shock promoters, and from the promoter normally associated with the PCPB sequence, provided such promoters are compatible with the host cell systems.

The early and late promoters of the SV40 virus are conveniently obtained as an SV40 restriction fragment that also contains the SV40 viral origin of replication. Fiers et al., *Nature*, 273:113 (1978); Mulligan and Berg, *Science*, 209: 1422–1427 (1980); Pavlakis et al., *Proc. Natl. Acad. Sci. USA*, 78: 7398–7402 (1981). The immediate early promoter of the human cytomegalovirus is conveniently obtained as a HindIII E restriction fragment. Greenaway et al., *Gene*, 18: 355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature*, 295: 503–508 (1982) on expressing cDNA encoding immune interferon in monkey cells, Reyes et al., *Nature*, 297: 598–601 (1982) on expression of human β-interferon cDNA in mouse cells under the control of a thymidine kinase promoter from herpes simplex virus, Canaani and Berg, *Proc. Natl. Acad. Sci. USA*, 79: 5166–5170 (1982) on expression of the human interferon β1 gene in cultured mouse and rabbit cells, and Gorman et el., *Proc. Natl. Acad. Sci. USA*, 79: 6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

Transcription of a DNA encoding the PCPB of this invention by higher eukaryotes is increased by inserting an enhancer sequence into the vector. Enhancers are cis-acting elements of DNA, usually about from 10 to 300 bp, that act on a promoter to increase its transcription. Enhancers are relatively orientation and position independent having been found 5′ (Laimins et el., *Proc. Natl. Aced. Sci. USA*, 78: 993 [1981]) and 3′ (Lusky et al., *Mol. Cell Bio.*, 3: 1108 [1983]) to the transcription unit, within an intron (Banerji et al., *Cell*, 33: 729 [1983]) as well as within the coding sequence itself (Osborne et el., *Mol. Cell Bio.*, 4: 1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature*, 297: 17–18 (1982) on enhancing elements for activation of eukaryotic promoters. The enhancer may be spliced into the vector at a position 5′ or 3′ to the PCPB-encoding sequence, but is preferably located at a site 5′ from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5′ and, occasionally 3′ untranslated regions of eukaryotic or viral DNAs or cDNAs. These regions contain nucleotide segments transcribed as polyadenylated fragments in the untranslated portion of the mRNA encoding PCPB. The 3′ untranslated regions also include transcription termination sites.

Suitable host cells for cloning or expressing the vectors herein are the prokaryote, yeast, or higher eukaryote cells described above. Suitable prokaryotes include eubacteria, such as Gram-negative or Gram-positive organisms, for example, *E. coli*, Bacilli such as *B. subtilis*, Pseudomonas species such as *P. aeruginosa*, *Salmonella typhimurium*, or *Serratia marcescans*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. Preferably the host cell should secrete minimal amounts of proteolytic enzymes. Alternatively, in vitro methods of cloning, e.g. PCR, are suitable.

In addition to prokaryotes, eukaryotic microbes such as filamentous fungi or yeast are suitable hosts for PCPB-encoding vectors. *Saccharomyces cerevisiae*, or common baker's yeast, is the most commonly used among lower eukaryotic host microorganisms. However, a number of other genera, species, and strains are commonly available and useful herein, such as *S. pombe* [Beach and Nurse, *Nature*, 290: 140 (1981)], *Kluyveromyces lactis* [Louvencourt et al., *J. Bacteriol.*, 737 (1983)], yarrowia [EP 402,226], *Pichia pastoris* [EP 183,070], *Trichoderma reesia* [EP 244,234], *Neurospora crassa* [Case et al., *Proc. Natl. Acad. Sci. USA*, 76: 5259–5263 (1979)], and Aspergillus hosts such as *A. nidulans* [Ballance et al., *Biochem. Biophys. Res. Commun.*, 112: 284–289 (1983); Tilburn et al., *Gene*, 26: 205–221 (1983); Yelton et al., *Proc. Natl. Acad. Sci. USA*, 81: 1470–1474 (1984)] and *A. niger* [Kelly and Hynes, *EMBO J.*, 4: 475–479 (1985)].

Suitable host cells for the expression of PCPB are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosphila melanogaster* (fruitfly), and *Bombyx mori* host cells have been identified. See, e.g., Luckow et al., *Bio/Technology*, 6:47–55 (1988); Miller et al., in *Genetic Engineering*, setlow, J. K. et al., eds., Vol. 8 (Plenum Publishing, 1986), pp. 277–279; and Maeda et al., *Nature*, 315: 592–594 (1985). A variety of such viral strains are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the PCPB DNA. During incubation of the plant cell culture with *A. tumefaciens*, the DNA encoding the PCPB is transferred to the plant cell host such that it is transfected, and will, under appropriate conditions, express the PCPB DNA. In addition, regulatory and signal sequences compatible with plant cells are available, such as the hopaline synthase promoter and polyadenylation signal sequences. Depicker et al., *J. Mol. Appl. Gen.* 1: 561 (1982). In addition, DNA segments isolated from the upstream region of the T-DNA 780 gene are capable of activating or increasing transcription levels of plant-expressible genes in recombinant DNA-containing plant tissue. EP 321,196 published 21 Jun. 1989.

However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36: 59 [1977]); baby hamster kidney cells (BHK, ATCC CCL 10); Chinese hamster ovary cells/-DHFR (CHO, Urlaub and Chasin, *Proc. Natl. Acad. Sci. USA,* 77: 4216 [1980]); mouse sertoli cells (TM4,Mather, *Biol. Reprod.*, 23: 243-251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383: 44-68 [1982]); MRC 5 cells; FS4 cells; and a human hepatoma line (Hep G2).

Construction of suitable vectors containing the desired coding and control sequences employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction, and/or sequenced by the method of Messing et al., *Nucleic Acids Res.*, 9: 309 (1981) or by the method of Maxam et al., *Methods in Enzymology*, 65: 499 (1980).

Most cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, CaPO$_4$ and electropotation. Successful transfection is generally recognized when any indication of the operation of this vector occurs within the host cell.

Transformation means introducing DNA into an organism so that the DNA is replicahie, either as an extrachromosomal element or by chromosomal integrant. Depending on the host cell used, transformation is done using standard techniques appropriate to such cells. The calcium treatment employing calcium chloride, as described by Cohen, *Proc. Natl. Acad. Sci. (USA),* 69: 2110 (1972) and Mandel et al., *J. Mol. Biol.* 53: 154 (1970), is generally used for prokaryotes or other cells that contain substantial cell-wall barriers.

Infection with *Agrobacterium tumefaciens* is used for transformation of certain plant cells, as described by Shaw et al., *Gene,* 23: 315 (1983) and WO 89/05859 published 29 Jun. 1989. For mammalian cells without such cell walls, the calcium phosphate precipitation method of Graham and van der Eb, *Virology,* 52: 456-457 (1978) is preferred. General aspects of mammalian cell host system transformations have been described by Axel in U.S. Pat. No. 4,399,216 issued 16 Aug. 1983. Transformations into yeast are typically carried out according to the method of Van Solingen et al., *J. Bact.*, 130: 946 (1977) and Hsiao et al., *Proc. Natl. Acad. Sci. (USA),* 76: 3829 (1979). However, other methods for introducing DNA into cells such as by nuclear injection or by protoplast fusion may also be used.

The mammalian host cells used to produce the PCPB of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.*, 58: 44 (1979), Barnes and Sato, *Anal. Biochem.*, 102: 255 (1980), U.S. Pat. Nos. 4,767,704; 4,657,866; 4,927,762; or 4,560,655; WO 90/03430; WO 87/00195; U.S. Pat. No. 30,985; or copending U.S. Ser. Nos. 07/592,107 or 07/592,141, both filed on 3 Oct. 1990, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin TM drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

It is further envisioned that the PCPB of this invention may be produced by homologous recombination, or with recombinant production methods utilizing control elements introduced into cells already containing DNA encoding the PCPB currently in use in the field. For example, a powerful promoter/enhancer element, a suppressor, or an exogenous transcription modulatory element is inserted in the genome of the intended host cell in proximity and orientation sufficient to influence the transcription of DNA encoding the desired PCPB. The control element does not encode the PCPB of this invention, but the DNA is present in the host cell genome. One next screens for cells making the PCPB of this invention, or for increased or decreased levels of expression, as desired.

Gene amplification and/or expression may be measured in a sample directly, for example, by conventional Southern blotting, Northern blotting to quantitate the transcription of mRNA (Thomas, *Proc, Natl. Acad. Sci.*

USA, 77: 5201–5205 [1980]), dot blotting (DNA analysis), or in situ hybridization, using an appropriately labeled probe, based on the sequences provided herein. Various labels may be employed, most commonly radioisotopes, particularly $^{32}$P. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75: 734–738 (1980).

Antibodies useful for immunohistochemical staining and/or assay of sample fluids may be either monoclonal or polyclonal. Conveniently, the antibodies may be prepared against a synthetic peptide based on the DNA sequences provided herein as described further below.

PCPB preferably is recovered from the culture medium as a secreted polypeptide, although it also may be recovered from host cell lysates when directly expressed without a secretory signal. When PCPB is expressed in a recombinant cell other than one of human origin, the PCPB is completely free of proteins or polypeptides of human origin. However, it is necessary to purify PCPB from recombinant cell proteins or polypeptides to obtain preparations that are substantially homogeneous as to PCPB. As a first step, the culture medium or lysate is centrifuged to remove particulate cell debris. PCPB thereafter is purified from contaminant soluble proteins and polypeptides, for example, by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel electrophoresis using, for example, Sephadex G-75; and chromatography on plasminogen columns to bind the PCPB and on protein A Sepharose columns to remove contaminants such as IgG.

PCPB variants in which residues have been deleted, inserted or substituted are recovered in the same fashion as native PCPB, taking account of any substantial changes in properties occasioned by the variation. For example, preparation of a PCPB fusion with another protein or polypeptide, e.g. a bacterial or viral antigen, facilitates purification because an immunoaffinity column containing antibody to the antigen can be used to adsorb the fusion. Immunoaffinity columns such as a rabbit polyclonal anti-PCPB column can be employed to absorb the PCPB variant by binding it to at least one remaining immune epitope. A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native PCPB may require modification to account for changes in the character of PCPB or its variants upon expression in recombinant cell culture.

PCPB also may be entrapped in microcapsules prepared, for example, by coacervation techniques or by interfacial polymerization (for example, hydroxymethylcellulose or gelatin-microcapsules and poly-[methylmethacylate] microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Osol, A., Ed., (1980).

PCPB is believed to find use as a hemostatic regulator for clotting blood, i.e., to coagulate blood, and particularly for treating mammals (e.g., animals or humans) *in vivo* having a blood clotting disorder such as hemophilia, especially hemophilia A. Hemophilia A is the result of Factor VIII deficiency, which mainly occurs in males. The disease is a major inherited bleeding disorder, occurring in about 0.01% of the male population. PCPB may be useful in cases where Factor VIII cannot be employed, as when the patient develops antibodies to Factor VIII.

PCPB preparations are also useful in generating antibodies, as standards in assays for PCPB such as by labeling PCPB for use as a standard in a radioimmunoassay, enzyme-linked immunoassay, or radioreceptor assay, in affinity purification techniques, and in competitive-type receptor binding assays when labeled with radioiodine, enzymes, fluorophores, spin labels, and the like.

Since it is often difficult to predict in advance the characteristics of a variant PCPB, it will be appreciated that some screening of the recovered variant will be needed to select the optimal variant. One can screen for plasminogen binding, enhanced carboxypeptidase activity, enhanced inhibition of plasminogen activation in the presence of a plasminogen activator and fibrinogen, stability in recombinant cell culture or in plasma (e.g. against proteolytic cleavage), possession of PCPB antagonist activity (e.g., enhancement of plasminogen activation in the presence of t-PA and fibrinogen), oxidative stability, ability to be secreted in elevated yields, and the like. For example, a change in the immunological character of the PCPB molecule, such as affinity for a given antibody, is measured by a competitive-type immunoassay. The variant is assayed for changes in the suppression or enhancement of its enzymatic activity by determining the kinetics of conversion of plasminogen to plasmin of the candidate mutant using the chromogenic plasmin substrate S-2251 in the presence of fibrinogen fragments and t-PA using the assay as described in the example below. Modifications of such protein or polypeptide properties as redox or thermal stability, hydrophobicity, susceptibility to proteolytic degradation, or the tendency to aggregate with carriers or into multimers are assayed by methods well known in the art.

Therapeutic formulations of PCPB for treating blood clotting disorders are prepared for storage by mixing PCPB having the desired degree of purity with optional physiologically acceptable carriers, excipients, or stabilizers (*Remington's pharmaceutical Sciences,* supra), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

PCPB to be used for in vivo administration must be sterile. This is readily accomplished by filtration through sterile filtration membranes, prior to or following lyophilization and reconstitution. PCPB ordinarily will be stored in lyophilized form.

Therapeutic PCPB compositions generally are placed into a container having a sterile access port, for example, an intravenous solution bag or vial having a stopper pierceable by a hypodermic injection needle.

PCPB optionally is combined with or administered in concert with other blood clotting agents including tissue factor and/or Factor VIII and is used with other conventional therapies for blood clotting disorders.

The route of PCPB or PCPB antibody administration is in accord with known methods, e.g. injection or infusion by intravenous, intraperitoneal, intracerebral, intramuscular, intraocular, intraarterial, or intralesional routes, or by sustained release systems as noted below. PCPB is administered continuously by infusion or by bolus injection. PCPB antibody is administered in the same fashion, or by administration into the blood stream or lymph.

Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al., *Biopolymers,* 22: 547-556 [1983]), poly (2-hydroxyethyl-methacrylate) (Langer et al., *J. Biomed. Mater. Res.,* 15: 167-277 [1981] and Langer, *Chem. Tech.,* 12: 98-105 [1982]), ethylene vinyl acetate (Langer et al., supra) or poly-D-(—)-3-hydroxybutyric acid (EP 133,988). Sustained-release PCPB compositions also include liposomally entrapped PCPB. Liposomes containing PCPB are prepared by methods known per se: DE 3,218,121; Epstein et al., *Proc. Natl. Acad. Sci. USA,* 82: 3688-3692 (1985); Hwang et al., *Proc. Natl, Acad, Sci. USA,* 77: 4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamelar type in which the lipid content is greater than about 30 mol. % cholesterol, the selected proportion being adjusted for the optimal PCPB therapy.

An effective amount of PCPB to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 $\mu$g/kg to up to 100 mg/kg or more, depending on the factors mentioned above. Typically, the clinician will administer PCPB until a dosage is reached that achieves the desired degree of clotting. The progress of this therapy is easily monitored by conventional assays.

Examples of treatment protocols that may be appropriate are those well known for Factor VIII, including those described in *Hematology* 1987, Education Program, American Society of Hematology, Washington, D.C. (5-8 Dec. 1987) and references cited therein; Sultan et al., *Nouv. Rev. Fr. Hematol.,* 28.: 85-89 (1986); Brackmann and Egli, *Hemophilia, London,* Castle House, pp. 113-119 (1981); Brackmann et al., *Lancet,* 2: 933 (1977); White et al., *Blood,* 62: 141-145 (1983); Van Leeuwen et al., *Br. J. Haematol.,* 64: 291-297 (1986).

Polyclonal antibodies to PCPB generally are raised in animals by multiple subcutaneous (sc) or intraperitoneal (ip) injections of PCPB and an adjuvant. It may be useful to conjugate PCPB or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic arthydride, $SOCl_2$, or $R^1N=C=NR$, where R and $R^1$ are different alkyl groups.

Animals are immunized against the immunogenic conjugates or derivatives by combining 1 mg or 1 $\mu$g of conjugate (for rabbits or mice, respectively) with 3 volumes of Freund's complete adjuvant and injecting the solution intradermally at multiple sites. One month later the animals are boosted with 1/5 to 1/10 the original amount of conjugate in Freund's complete adjuvant by subcutaneous injection at multiple sites. 7 to 14 days later animals are bled and the serum is assayed for anti-PCPB titer. Animals are boosted until the titer plateaus. Preferably, the animal is boosted with the conjugate of the same PCPB, but conjugated to a different protein and/or through a different cross-linking agent. Conjugates also can be made in recombinant cell culture as protein fusions. Also, aggregating agents such as alum are used to enhance the immune response.

Monoclonal antibodies are prepared by recovering spleen cells from immunized animals and immortalizing the cells in conventional fashion, e.g. by fusion with myeloma cells or by Epstein-Barr (EB)-virus transformation and screening for clones expressing the desired antibody. The monoclonal antibody preferably does not cross-react with a carboxypeptidase A, B, E, M, or N, a non-plasma derived carboxypeptidase B, or a non-mammalian carboxypeptidase.

PCPB antibodies are useful in diagnostic assays for PCPB. The antibodies are labeled in the same fashion as PCPB described above and/or are immobilized on an insoluble matrix. In one embodiment of a receptor binding assay, an antibody composition that binds to all or a selected plurality of members of the PCPB family is immobilized on an insoluble matrix, the test sample is contacted with the immobilized antibody composition to adsorb all PCPB family members, and then the immobilized family members are contacted with a plurality of antibodies specific for each member, each of the antibodies being individually identifiable as specific for a predetermined family member, as by unique labels such as discrete fluorophores or the like. By determining the presence and/or amount of each unique label, the relative proportion and amount of each family member can be determined.

PCPB antibodies also are useful for the affinity purification of PCPB from recombinant cell culture or natural sources. PCPB antibodies that do not detectably cross-react with other carboxypeptidases such as pancreas, mast cell, and plasma carboxypeptidase A, non-plasma derived B, or carboxypeptidases N, E, or M or non-mammalian carboxypeptidases can be used to purify PCPB free from these other carboxypeptidases.

Suitable diagnostic assays for PCPB and its antibodies are well known per se. In addition to the bioassays described above and in the examples wherein the candidate PCPB is tested to see if it inhibits plasmin activity and the activation of plasminogen in the presence of t-PA and fibrinogen, competitive, sandwich and steric inhibition immunoassay techniques are useful. The competitive and sandwich methods employ a phase-separation step as an integral part of the method while steric inhibition assays are conducted in a single reaction mixture. Fundamentally, the same procedures are used for the assay of PCPB and for substances that bind PCPB, although certain methods will be favored depending upon the molecular weight of the substance being assayed. Therefore, the substance to be tested is referred to herein as an analyte, irrespective of its status otherwise as an antigen or antibody, and proteins that bind to the analyte are denominated binding partners, whether they be antibodies, cell surface receptors, or antigens.

Analytical methods for PCPB or its antibodies all use one or more of the following reagents: labeled analyte analogue, immobilized analyte analogue, labeled binding partner, immobilized binding partner and steric conjugates. The labeled reagents also are known as "tracers."

The label used (and this is also useful to label PCPB nucleic acid for use as a probe) is any detectable functionality that does not interfere with the binding of analyte and its binding partner. Numerous labels are known for use in immunoassay, examples including moieties that may be detected directly, such as fluorochrome, chemiluminscent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferass and bacterial luciferass (U.S. Pat. No. 4,737,456), luciferin, 2,3-dihydrophthalazinediones, horseradish peroxidase (HRP), alkaline phosphatase, $\beta$-galactosidase, glucoamylase, lysozyme, saccharide oxidases, e.g., glucose oxidase, galacrose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. Nos. 3,940,475 (fluorimetry) and 3,645,090 (enzymes); Hunter et al., Nature, 144: 945 (1962); David et al., Biochemistry, 13: 1014–1021 (1974); Pain et al., J. Immunol. Methods, 40: 219–230 (1981); and Nygren, J. Histochem. and Cytochem., 30: 407–412 (1982). Preferred labels herein are enzymes such as horseradish peroxidase and alkaline phosphatase.

The conjugation of such label, including the enzymes, to the antibody is a standard manipulative procedure for one of ordinary skill in immunoassay techniques. See, for example, O'Sullivan et al., "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, New York, 1981), pp. 147–166. Such bonding methods are suitable for use with PCPB or its antibodies, all of which are proteinaceous.

Immobilization of reagents is required for certain assay methods. Immobilization entails separating the binding partner from any analyte that remains free in solution. This conventionally is accomplished by either insolubilizing the binding partner or analyte analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the partner or analogue afterward, e.g., by immunoprecipitation.

Other assay methods, known as competitive or sandwich assays, are well established and widely used in the commercial diagnostics industry.

Competitive assays rely on the ability of a tracer analogue to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results to quantitatively determine the amount of analyte present in the test sample. These assays are called ELISA systems when enzymes are used as the detectable markers.

Another species of competitive assay, called a "homogeneous" assay, does not require a phase separation. Here, a conjugate of an enzyme with the analyte is prepared and used such that when anti-analyte binds to the analyte the presence of the anti-analyte modifies the enzyme activity. In this case, PCPB or its immunologically active fragments are conjugated with a bifunctional organic bridge to an enzyme such as peroxidase. Conjugates are selected for use with anti-PCPB so that binding of the anti-PCPB inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small analyte so that antibody to hapten substantially is unable to bind the conjugate at the same time as anti-analyte. Under this assay procedure the analyte present in the test sample will bind anti-analyte, thereby allowing anti-hapten to bind the conjugate, resulting in a change in the character of the conjugate hapten, e.g., a change in fluorescence when the hapten is a fluorophore.

Sandwich assays particularly are useful for the determination of PCPB or PCPB antibodies. In sequential sandwich assays an immobilized binding partner is used to adsorb test sample analyte, the test sample is removed as by washing, the bound analyte is used to adsorb labeled binding partner, and bound material is then separated from residual tracer. The amount of bound tracer is directly proportional to test sample analyte. In "simultaneous" sandwich assays the test sample is not separated before adding the labeled binding partner. A sequential sandwich assay using an anti-PCPB monoclonal antibody as one antibody and a polyclonal anti-PCPB antibody as the other is useful in testing samples for PCPB activity.

The foregoing are merely exemplary diagnostic assays for PCPB and antibodies. Other methods now or hereafter developed for the determination of these analytes are included within the scope hereof, including the bioassays described above.

The following examples are offered by way of illustration and not by way of limitation. All literature references cited in the example section are expressly incorporated herein by reference.

EXAMPLE I

Purification of PCPB

A total of 20 units of human plasma was batch separated with 1 liter of lysine-Sepharose (Pharmacia) pre-equilibrated with phosphate buffered saline (PBS). After 2 hours at 4° C. the resin was removed by centrifugation. The plasminogen-depleted plasma was made 0.8M with ammonium sulfate and subsequently centrifuged at 10,000×g for 30 min. The pellet was discarded and the supernatant was made 2.7M ammonium sulfate and re-centrifuged. The supernatant was discarded and the 2.7M pellet was dissolved in PBS and extensively dialyzed against the same.

After dialysis, the 2.7M pellet was chromatographed on a plasminogen affinity column, prepared by coupling plasminogen to glycerol-coated control pore glass at 15 mg/g as described by Roy et al., *J. Chromatography,* 303: 225–228 (1984). The column was washed with 10 column volumes of PBS and eluted with PBS containing 0.2M of epsilon-aminocaproic acid (EACA). Fractions containing PCPB (identified by SDS-PAGE and amino acid sequence) were pooled, made 1M NaCl, and passed over a protein-A Sepharose column (Pharmacia) equilibrated in PBS to remove contaminating IgG. Fractions containing PCPB identified as described above were pooled and re-chromatographed on the plasminogen affinity column. The column was washed with 10 column volumes of PBS and eluted with a 0–50 mM gradient of EACA and the fractions containing PCPB (identified as described above) were recovered.

SDS-PAGE of PCPB before and after protein-A Sepharose purification revealed a band at a molecular weight of about 60 kD on both a reducing and non-reducing gel. Sequencing by Edman degradation of the polypeptide before protein-A Sepharose purification gave the following N-terminal sequence:

PheGlnSerGlyGlnValLeuAlaAlaLeuProArgThrSerArgGlnValGlnVal—
LeuGlnAsnLeuThrThrThrTyrGluIleValLeuArgGluProValThrAla.
(Sequence ID No. 1)

The purified PCPB was tested to determine its effect on plasminogen activation. The plasmin-specific substrate H-D-valyl-H-leucyl-H-lysine-paranitroanilide (S-2251) was used in a two-stage assay to measure the ability of the sample to activate plasminogen. Human fibrinogen (Calbiochem) was made plasminogen free by applying it to a lysine-Sepharose column and collecting the flow-through. The fibrinogen was used as a stimulator by incubating 450 mm of the PCPB sample with 1800 nM fibrinogen and 815 nM Glu-plasminogen solution (commercially available) in 50 mM TrisOH, pH 7.5, buffer containing 0.15M NaCl and 0.01% Tween 20 (TBST) at a final volume of 0.3 ml for 5 minutes at 37° C. Subsequently, 0.1 ml of TBST containing 25 ng of human rt-PA (Activase ® brand alteplase, Genentech, Inc.) was added and the mixture was incubated another 10 minutes at 37° C. Plasmin generated was then determined by the addition of S-2251 to a final concentration of 1 mM. After 10 min. at 37° C. 0.1 ml of 50% glacial acetic acid was added to quench the reaction and absorbance at 405 nm was determined.

The maximum rate of this reaction was observed in the absence and presence of fibrinogen that acts as a stimulator of the reaction. Also, control samples were run without the PCPB.

The optical density at 405 nm is shown for these experiments in FIG. 1. It can be seen that PCPB blocks the action of t-PA in converting plasminogen to plasmin only in the presence of fibrinogen.

The purified PCPB was also tested to determine its effect on plasmin activity. 3.6 nM plasmin (Helena Labs) was incubated with either PCPB (303 nM) or anti-plasmin (American Diagnostic) (256 nM) for 15 minutes at 37° C., and plasmin activity was determined by the S-2251 assay described above. The results, shown in FIG. 2, where "CONT." indicates control (plasmin alone) and "AP" indicates anti-plasmin, demonstrate that PCPB does not block the action of plasmin.

EXAMPLE II

Cloning and Expression of PCPB DNA Cloning

Attempts to identify and isolate DNA encoding PCPB from a human liver cDNA library using two probes based on the 37 residues of amino-terminal amino acid sequence obtained from plasma-derived PCPB were unsuccessful. Specifically, the initial strategy was to design two long oligonucleotide probes, 45 and 63 bases in length, each representing a single, non-degenerate sequence encoding a portion of the 37 amino acid sequence [the 45-met encoded amino acids 16–29 and the 63-mer encoded amino acids 1–19]. These probes were labeled and used to screen a human liver cDNA library in the vector lambda gt10 [Ullrich et al., *Nature,* 309: 418–425 (1984); Huynh et al., in *DNA Cloning, A practical Approach,* ed. Glover, D. (IRL, Oxford), Vol. 1, pp. 49–78 (1985)]. The 63-mer hybridized to some 20 clones out of a million at normal stringency, and the 45-mer hybridized to zero out of a million clones. The clones that hybridized to the 63-mer had long (up to 4.5 kb) inserts, none of which encoded a protein with the known amino-terminal amino acid sequence of PCPB. The conclusion from these experiments was that cloning PCPB by the standard technique of probing cDNA libraries with a single long oligonucleotide was a failure.

Instead, to identify the PCPB gene, it was necessary to amplify human cDNA using PCR (Mullis et al., Cold Spring Harbor Symp. Quant. Biol., 51:263 [1987]). Three groups of highly degenerate PCR primers were designed. All primers were 26 bases in length. Primer pools pbp.8 and pbp.9 were 16,384-fold and 49,152-fold degenerate, respectively, and represented all possible coding sequences for the first 9 and last 9 amino acids of the 37-amino-acid sequence. Primer pbp. 10 was 24,576-fold degenerate, and was internal to pbp.8 and pbp.9. This primer represented all possible coding sequences for amino acids 9-17 of the known sequence. The expected PCR product from primers pbp.8 and pbp.9 was 105 bp., while the expected PCR product from primers pbp.8 and pbp.10 was 95 bp. in length.

Human mRNA was used as the initial starting material for PCR. RNA extracted from human liver and kidney by known procedures [for example, as described in Section 7.3 of Sambrook et al., supra] was reverse transcribed to cDNA with reverse transcriptase using known techniques as described in Section 8.3-8.53 of Sambrook et al., supra. Both single-stranded and double-stranded cDNA [the latter prepared as described by Sambrook et al.] was amplified with the degenerate primer pools. The conditions for amplification were as follows:

| denat. | 95° C. 5' | once initially |
|---|---|---|
| denat. | 95° C. 1' | |
| anneal | 50° C. 1' | 30 cycles |
| extens. | 72° C. 1' | |
| extens. | 72° C. 15' | |

10 μl 10× buffer (final = 50 mM KCl, 10 mM Tris pH 8.4, 3.0 mM MgCl$_2$)
3 μl human cDNA (3 μg)
7.5 ng/μl primer pbp.8 (approx. 1 μg = ~ 2.6 μM of 26 mer, therefore 10$^3$ degen = nM, 10$^6$ = pM)
7.5 ng/μl primer pbp.9
7.5 ng/μl primer pbp.10
10 μl 10× dNTPs (final = 0.2 mM dNTPs)
1 μl Taq polymerase
61 μl dH$_2$O
107.5 μl V$_T$ (total volume)

No PCR products of the correct expected size were produced.

A bi-phasic PCR protocol was then utilized, in which the first 10 cycles of amplification were carried out at 50° C. annealing temperature and the subsequent 20 cycles of amplification were carried out at reduced (40° C.) stringency. In addition, the product of the reaction using the outermost primers (pbp.8 and pbp.9) was subjected to a second round of bi-phasic PCR using the more internal primers (pbp.8 and pbp.10). This second round of PCR amplification produced, along with a large number of other PCR products, the expected 95-bp band from liver, but not from kidney, cDNA.

Figure 3:
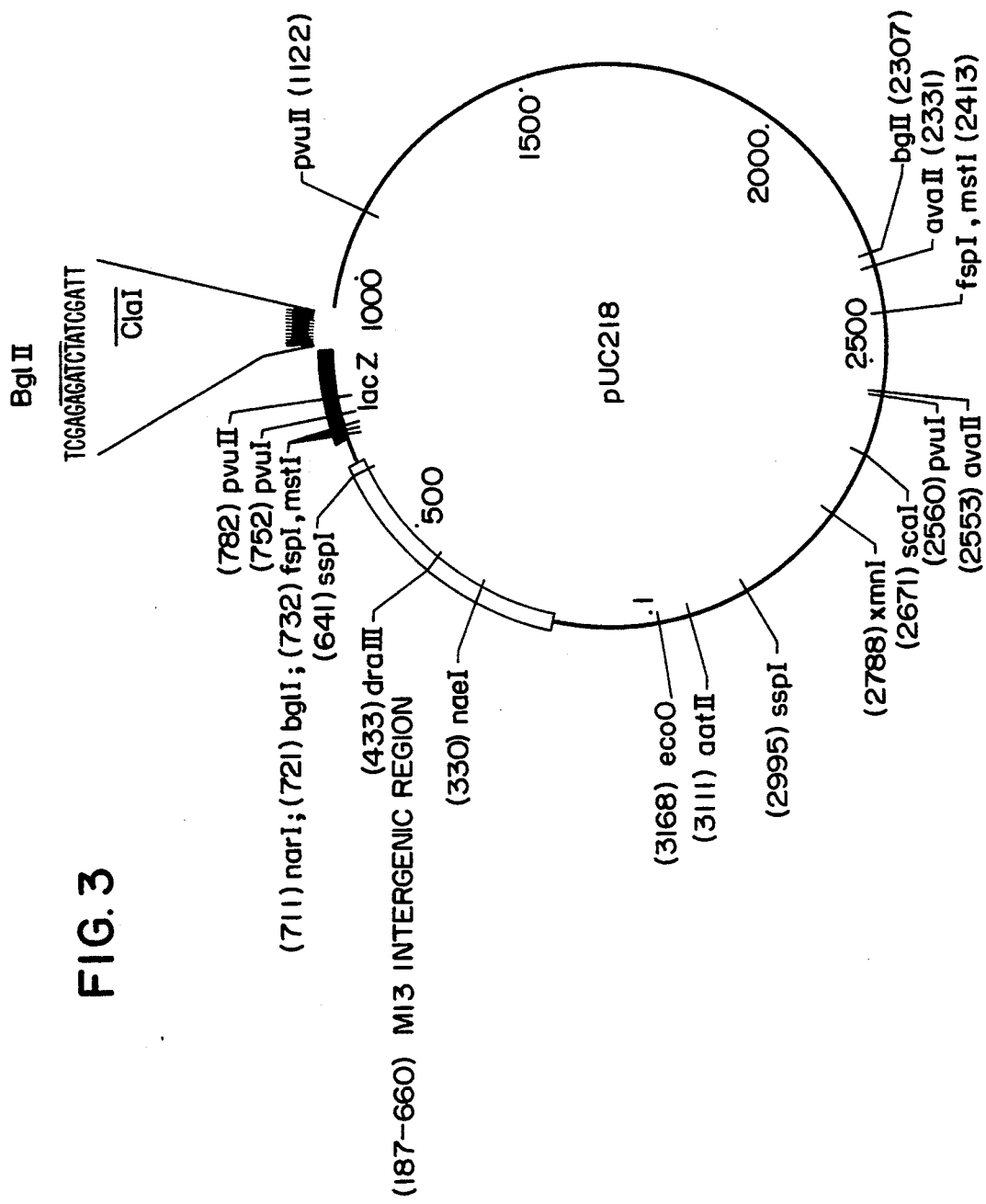
FIG. 3 illustrates a restriction map of pUC218, which is prepared by inserting the indicated nucleotides into the designated site of pUC118.

This 95-bp PCR product was cloned into pUC218 (prepared by ligating the nucleotides TCGAGA-GATCTATCGATT into the vector pUC 118 at the location indicated in FIG. 3) and sequenced. pUCl18 is described by Vieira and Messing, Meth. Enzymol., 153: 3-11 (1987). Briefly, pUC118 is a 3.2 kb plasmid with ampicillin resistance and M13 IG region, and a sequence encoding the lacZ peptide containing unique restriction sites for cloning. pUC118 is pUC18 (Norrander et al., Gene, 26: 101 [1983]) with the IG region of M13 from the HgiAI site (5465) to the DraI site (5941) inserted at the unique NdeI site (2499) of pUC. The orientation of the M13 IG region is such that the strand of the lac region that is packaged as ssDNA is the same as in the M13mp vectors.

The DNA sequence of the PCR product, which is shown in FIG. 4 (Sequence ID No. 2), was capable of encoding the sequenced first 37 amino acids of PCPB (with the exception of the Trp at position 27, which was in error). Since this PCR product was obtained using highly degenerate primers, the DNA sequence at the ends that contain these primers could not be assumed to be identical to the authentic mRNA sequence for PCPB. Therefore, for full-length clones, a single 46-bp oligonucleotide probe from the interior region of this 95-bp sequence was synthesized, having the sequence spanning the nucleotides shown in FIG. 4, i.e. 133 to 178. This probe was radiolabeled using conventional techniques and hybridized at high stringency [50% formamide, 5×SSC (0.75M NaCl, 0.075M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washing at 42° C. in 0.2×SSC and 0.1% SDS] to a human liver cDNA library in the vector lambda gt10 as described above.

A total of 110 positives were obtained from 1.3 million clones (thus, positive clones appeared at a frequency of 0.008%). Five of these positive clones, assigned the designation PBP that is equivalent to PCPB [PBP1a, PBP1b, PBP2a, PBP2b, and PBP2c], were purified and grown up, and their cDNA inserts were subcloned into pUC218. One subclone, PBP1b (deposited with the ATCC as ATCC No. 40,927), was sequenced as double-stranded supercoiled templates, using both universal primers and specific internal synthesized primers as described in Section 13.70 of Sambrook et al., supra. Portions of other clones were partially sequenced by the same method, using universal primers.

DNA sequencing revealed that at least 4 out of these 5 clones represented different clones of the same gene. The DNA sequence predicts a single open reading frame 1269 bases long, from which is deduced a primary translation product 423 amino acids in length. Flanking this open reading frame are ca. 150 bp of 5' untranslated sequence and 421 bp of 3' untranslated sequence, which include the polyadenylation signal AATAAA 22 bp upstream from a poly A tail. Following the initiator methionine, there is a sequence 22 amino acids long that is not contained in PCPB. This sequence contains several features common to known signal peptides, including a generally hydrophobic character and a terminal alanine, after which begins the amino-terminal sequence found in PCPB.

Searches of DNA and protein sequence databases (Genbank and Dayhoff, respectively) reveal that this novel polypeptide has substantial sequence identity with known carboxypeptidases, including rat pancreas carboxypeptidase A1 and A2, rat pancreas carboxypeptidase B, bovine pancreas carboxypeptidase B, and both murine and human mast cell carboxypeptidase A. The greatest homologies were found with carboxypeptidases A and B, and a comparison of the sequence of preprohPCPB (Sequence ID No. 3) with the known sequences of prepro-rat carboxypeptidase B (Sequence ID No. 4), prepro-rat carboxypeptidase A1 (Sequence ID No. 5), prepro-human mast cell carboxypeptidase A (Sequence ID No. 6), prepro-mouse mast cell carboxypeptidase A (Sequence ID No. 7), and prepro-rat carboxypeptidase A2 (Sequence ID No. 8) is shown in FIG. 5. Overall, there is about 40% sequence identity at the amino acid level between preprohPCPB and prepro-human mast cell carboxypeptidase A, and between preproPCPB and prepro-rat carboxypeptidase B.

In particular, there is identity at three of four amino acids that form the catalytic site, at five of seven amino acids that form the substrate binding pocket, and at four cysteine residues known to form intramolecular disulfide bonds in two pairs in mast cell carboxypeptidase A (Reynolds et al., *J. Biol. Chem.*, 264: 20094–99 [1989]).

Human PCPB shares a small amount of sequence identity with human plasma carboxypeptidases N, M, and E (e.g., positions 232 to 237 of mature hPCPB correspond to positions 138–143 of the human carboxypeptidase N 48–55 kD subunit whose sequence is shown in FIG. 6 of Tan et al., *J. Biol. Chem.*, supra, spanning from Asp to Phe). In addition, human PCPB has the same substrate binding sites as, and shares a fifth and sixth cysteine residue with, bovine and rat carboxypeptidase B. These cysteines form a third intramolecular disulfide bond that is not present in human mast cell carboxypeptidase A. Also, the serine cleavage site that is cleaved to form proteolytically active rat cell carboxypeptidase B when activated by trypsin also exists in PCPB in an analogous position (Arg residue at position 92). All of these features strongly suggest that PCPB is a functional carboxypeptidase. Because hPCPB has the same amino acid (aspartic acid at position 348) at the region in carboxypeptidases that determines substrate specificity as carboxypeptidase B (Asp), it is believed that PCPB represents a plasma-derived carboxypeptidase B.

Expression

The following protocol for expressing PCPB DNA and purifying the resultant PCPB is expected to provide sufficient PCPB for assay purposes.

A cytomegalovirus-based expression vector called pRK5, described in Gorman et al., *DNA and Protein Engineering Techniques*, 2: 1 (1990) and in EP 307,247 published 15Mar. 1989, was employed as the expression vector. The PCPB cDNA insert from clone PBP.1b was cut from pUC218 in which it was cloned using partial EcoRI digest to obtain the −1.7 kb insert fragment. This DNA fragment was then ligated into pRK5 previously cut with EcoRI to accommodate the DNA fragment using standard ligation methodology as described in Sections 5.10 to 5.11 of Sambrook et al., supra. The resulting vector was called pRK-5hPBP.1b.

Human embryonic kidney 293 cells (Graham et al., *J. Gen. Virol.*, 36: 59 [1977], subclone 293TSA transfected with the temperature-sensitive large T-antigen gene) were grown to 70% confluence in 6-well plates in a DMEM:F12 (1:1) medium containing 1 mM HEPES buffer, 0.29 g/l glutamine, 2.44 g/l sodium bicarbonate, 0.55 g/l sodium pyruvate, pH 6.95, supplemented with 10% whole fetal calf serum. The day before the transfection the cells were counted, the medium was aspirated off, and the cells were trypsinized and resuspended in the same DMEM:F12 (1:1)-based medium containing 10% whole fetal calf serum that had been run through a lysine-containing column to remove plasminogen. Then the suspension was adjusted to 266,000 cells/ml, seeded at 3 ml per well of a six-well plate (800,000 cells/well), and incubated until the day of the transfection.

A total of 5 $\mu$g of the plasmid DNA (pRK-5hPBP.1b) was dissolved in 150 $\mu$l of 1 mM Tris-HCl, 0.1 mM EDTA, 0,227M CaCl$_2$. Added to this (dropwise while vortexing) was 150 mM $\mu$l of 50 mM HEPES buffer (pH 7.35), 280 mM NaCl, 1.5 mM NaPO$_4$, and the precipitate was allowed to form for ten min. at 25° C. The suspended precipitate was then added to the cells in the 60-mm tissue culture plate and allowed to settle overnight in the incubator. The medium was then aspirated off and replaced with DMEM:F12 (1:1)-based serum-free medium called PS-04 containing insulin, transferrin, trace elements, and lipids and described in U.S. Ser. No. 07/592,141, supra.

After the cells were incubated for four hours in the presence of 200 $\mu$Ci/ml $^{35}$S-cysteine and 200 $\mu$Ci $^{35}$S-methionine, conditioned medium was then collected, concentrated 5-fold by lyophilization, and loaded on a 15% SDS gel, which was subsequently enhanced, dried, and exposed to film for two hours. Because of an interfering protein, it could not be determined from the gel whether a polypeptide of approximately the expected size (60 kD) was obtained.

It is expected that a polypeptide of the correct molecular size would be detected if the transfection medium were placed on a plasminogen affinity column as described above washed with 10 column volumes of PBS and eluted with a 0 to 50 mM EACA gradient to remove the interfering contaminant, followed preferably by protein A-Sepharose column chromatography as described above.

Large-scale expression of PCPB is performed by transiently introducing by the dextran sulfate method (Sompayrac and Danna, *Proc. Natl. Acad. Sci. USA*, 12: 7575 [1981]) 700 $\mu$g of pRK-5hPBP.1b into the human embryonal kidney 293 cell line grown to maximal density (1.5 liters) in a 3-liter Belco microcarrier spinner flask. The cells are first concentrated from the spinner flask by centrifugation, and washed with PBS, and the DNA-dextran precipitate is incubated on the cell pellet for four hours. The cells are treated with 20% glycerol for 90 seconds, washed with a medium such as 50:50 DMEM:F-12 medium, and reintroduced into a 3-liter spinner flask containing 1.5 liter of the above medium plus 5 $\mu$g/ml bovine insulin and 0.1 $\mu$g/ml bovine transferrin. The above protocol is performed for three separate 3-liter cultures.

In a different expression protocol, pRK-5hPBP.1b was transfected into COS cells using the same conditions as for the 293 cells described above.

For larger-scale production of PCPB, the preferred vector is a SV40-driven vector such as pSVI6B described above, the preferred host cells are Chinese hamster ovary cells.

Deposit of Materials

The following plasmid DNA has been deposited with the American Type Culture Collection, 12301 Parklawn Drive, Rockville, Md., USA (ATCC):

| Plasmid DNA | ATCC Accession No. | Deposit Date |
|---|---|---|
| pPBP.lb | 40,927 | 29 Nov. 1990 |

This deposit was made under the provisions of the Budapest Treaty on the International Recognition of the Deposit of Microorganisms for the Purpose of Patent Procedure and the Regulations thereunder (Budapest Treaty). This assures maintenance of a viable deposit for 30 years from the date of deposit. The plasmid DNA will be made available by ATCC under the terms of the Budapest Treaty, and subject to an agreement between Genentech, Inc. and ATCC, which assures permanent and unrestricted availability of the plasmid DNA to the public upon issuance of the pertinent U.S. patent or upon laying open to the public of any U.S. or foreign patent application, whichever comes first, and assures availability of the plasmid DNA to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the deposited DNA should be lost or destroyed when transformed into a suitable host cultivated under suitable conditions, it will be promptly replaced on notification with a specimen of the same DNA. Availability of the deposited DNA is not to be construed as a license to practice the invention in contravention of the rights granted under the authority of any government in accordance with its patent laws.

The foregoing written specification is considered to be sufficient to enable one skilled in the art to practice the invention- The present invention is not to be limited in scope by the plasmid DNA deposited, since the deposited embodiment is intended as a single illustration of one aspect of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

What is claimed is:

1. An isolated nucleic acid molecule encoding monomeric human plasma carboxypeptidase B having in its mature form the N-terminal sequence PheGlnSer.

2. The nucleic acid molecule of claim 1 having the translated portion of the DNA sequence shown in FIG. 4 and in SEO ID NO:2.

3. The nucleic acid sequence of claim 1 that encodes a polypeptide having the translated portion of the amino acid sequence shown in FIG. 4 and in SEO ID NO;2.

4. An expression vector comprising the nucleic acid molecule of claim 1 operably linked to control sequences recognized by a host transformed by the vector.

5. A host cell transformed with the vector of claim 4.

* * * * *